United States Patent [19]
Ando et al.

[11] Patent Number: 5,357,198
[45] Date of Patent: Oct. 18, 1994

[54] APPARATUS FOR MAGNETIC INSPECTION USING MAGNETIC SHIELD

[75] Inventors: Seigo Ando; Yasuhiro Matsufuji, both of Tokyo, Japan

[73] Assignee: NKK Corporation, Tokyo, Japan

[21] Appl. No.: 927,498

[22] PCT Filed: Jan. 31, 1992

[86] PCT No.: PCT/JP92/00096
    § 371 Date: Sep. 29, 1992
    § 102(e) Date: Sep. 29, 1992

[87] PCT Pub. No.: WO92/14145
    PCT Pub. Date: Aug. 20, 1992

[30] Foreign Application Priority Data

Feb. 4, 1991 [JP] Japan ................................ 3-013568
Feb. 18, 1991 [JP] Japan ............................... 3-023306
Feb. 18, 1991 [JP] Japan ............................... 3-023307

[51] Int. Cl.⁵ .................... G01N 27/83; G01R 33/12
[52] U.S. Cl. ..................................... 324/242; 324/225; 324/262
[58] Field of Search ............... 324/225, 235, 240–243, 324/262

[56] References Cited

U.S. PATENT DOCUMENTS 5,021,738 6/1991 Vernon et al. ...................... 324/232
5,089,776 2/1992 Furukawa et al. ............. 324/262 X

FOREIGN PATENT DOCUMENTS 597671    5/1934  Fed. Rep. of Germany ...... 324/240
50-11087  2/1975  Japan .
60-20708  5/1985  Japan .
1-148856 10/1989  Japan .
2-30051   2/1990  Japan .
1302150   4/1987  U.S.S.R. ........................... 324/240

*Primary Examiner*—Gerard R. Strecker
*Attorney, Agent, or Firm*—Frishauf, Holtz, Goodman & Woodward

[57] ABSTRACT

In a magnetic inspection method and apparatus, a magnetizer (4) is provided such that a pair of magnetic poles (4a, 4b) face an object (10) to be inspected. A magnetic field is generated by the magnetizer (4) in the object (10). A magnetic sensor (7a) is situated at a substantially middle point of a line connecting the magnetic poles (4a, 4b) or a line parallel to this connecting line. Shield bodies (22a, 22b, 23a, 23b) with a low coercive force are arranged on those sides of the magnetic sensor (10) which face the magnetic poles. The magnetic sensor (7a) detects a leakage magnetic flux due to an internal or surface defect of the object (10). In addition, the distance (2A) between the shield bodies (22a, 22b) is 2.2 times or more, and 2.8 times or less, the distance (L) between the magnetic sensor (7a) and the object (10). Furthermore, each shield body (23a, 23b) has an L-cross section composed of a vertical portion (24a) and a horizontal portion (24b), and the width (2A) of the horizontal portion (24b) in the direction of arrangement of the magnetic poles (4a, 4b) is 0.4 time or more, and 0.6 time or less, the distance (B) between the magnetic poles.

14 Claims, 26 Drawing Sheets

APPARATUS FOR MAGNETIC INSPECTION USING MAGNETIC SHIELD

Technical Field

The present invention relates to a magnetic inspection method and a magnetic inspection apparatus wherein a magnetic field is generated by a magnetizer in a to-be-inspected object formed of a magnetic material such as steel plate and a leakage magnetic flux due to a defect on the object is detected by a magnetic sensor.

BACKGROUND ART

A magnetic inspection apparatus detects, by utilizing magnetism, defects such as internal and surface flaws and inclusion in a thin steel strip or a to-be-inspected object. It was reported that a magnetic inspection apparatus, in which a magnetic sensor array comprising linearly arranged magnetic sensors for detecting magnetic fluxes is built, is capable of successively detecting defects on a running thin steel strip over the entire width thereof (Published Unexamined Japanese Utility Model Application (PUJUMA No. 63-107849).

FIGS. 39 and 40 are schematic cross-sectional views showing, in different directions, the above-mentioned magnetic inspection apparatus for successively detecting the defects on the running thin steel strip. FIG. 41 is a side view showing the state in which the magnetic inspection apparatus is built in a support apparatus.

Referring to FIG. 41, a horizontal arm 12 is supported by a pair of spring members 13a and 13b within a frame 11 set on the floor of a room. Accordingly, the arm 12 is vertically movable. A stationary shaft 2 of the magnetic inspection apparatus is fixed at the center of the arm 12. A pair of guide rolls 14a and 14b for guiding a thin steel strip 10 on the outer peripheral surface of a hollow roll 1 are arranged on both sides of the frame 11.

In FIGS. 39 and 40, one end portion of the stationary shaft 2 penetrates the hollow roll 1 of a non-magnetic material along the center axis of the roll 1. The other end portion of the shaft 2 is fixed on the horizontal arm 12. The stationary shaft 2 is supported on the inner peripheral surfaces of both end portions of the hollow roll 1 by a pair of rolling bearings 3a and 3b such that the shaft 2 is situated along the center axis of the hollow roll 1. Accordingly, the hollow roll 1 is freely rotatable about the stationary shaft 2.

A magnetizing core 4c having a substantially U-cross section is fixed to the stationary shaft 2 by means of a support member 5 within the hollow roll 1, such that magnetic poles 4a and 4b of the core 4c are situated close to the inner peripheral surface of the hollow roll 1. A magnetizing coil 6 is wound around the magnetizing core 4c. Thus, the magnetizing core 4c and magnetizing coil 6 constitute a magnetizer 4. A magnetic sensor array 7 consisting of magnetic sensors 7a arranged linearly along the axis of the hollow roll 1 is fixed to the stationary shaft 2 between the magnetic poles 4a and 4b of the magnetizing core 4c.

A power cable 8 for supplying an excitation current to the magnetizing coil 6 and a signal cable 9 for taking out output signals from the magnetic sensors 7a of the magnetic sensor array 7 are led to the outside through the inside passage of the stationary shaft 2. Accordingly, the positions of the magnetizer 4 and magnetic sensor array 7 are fixed, and the hollow roll 1 rotates around the magnetizer 4 and magnetic sensor array 7 with a small gap.

when the outer peripheral surface of the hollow roll 1 of the magnetic inspection apparatus with the above structure is pressed on one side surface of the thin steel strip 10 under a predetermined pressure which runs, for example, in a direction a, the hollow roll 1 rotates in a direction b since the stationary shaft 2 is fixed on the horizontal arm 12.

In the above magnetic inspection apparatus, when an excitation current is supplied to the magnetizing coil 6, a closed magnetic path is formed by the magnetic poles 4a and 4b of the magnetizing core 4c and the running thin steel strip 10. If there is an internal or surface defect of the thin steel strip, the magnetic path in the thin steel strip is disturbed and a leakage magnetic flux occurs. The leakage magnetic flux is detected by the magnetic sensor 7a which constitutes a part of the magnetic sensor array 7 and faces the location of the defect. A signal corresponding to the defect is output from this magnetic sensor 7a.

The level of this output detection signal corresponds to the magnitude of the internal or surface defect of the thin steel strip 10. Thus, by measuring the level of the output signal, the width, directional position and magnitude of the internal or surface defect of the steel strip 10 can be determined.

However, regarding the above-described magnetic inspection apparatus, there are the following problems to be solved.

When a small defect of the object such as the thin steel strip 10 is detected, the S/N does not basically increase unless the magnetic force is adequate.

In order to solve such a problem, there is an idea that the excitation current to the magnetizing coil 6 of the magnetizer 4 is increased to intensify the magnetic field forming in the thin steel strip 10. The greater the magnetic flux in the steel strip 10, the higher the value of the leakage magnetic flux due to the defect.

In general, as shown in FIG. 42, when the magnetic poles 4a and 4b are situated near the thin steel strip 10, magnetic force lines extend from the pole 4a to the pole 4b through a magnetic gap, the thin steel plate 10 and another magnetic gap. Since the thin steel strip 10 is formed of a ferromagnetic material, magnetic fluxes do not leak out of the thin steel strip 10 while passing through the strip 10 if no defect is present in the strip 10.

However, as stated above, if the magnetic field applied to the thin steel strip 10 is increased so as to obtain a leakage magnetic flux of a sufficiently high signal level when a defect is present, the strip 10 is magnetically saturated, as shown in FIG. 42. As a result, a large floating magnetic flux 15 occurs even in a defect-free portion. The actual value of the floating flux 15 is extremely high, e.g. several Gauss to several-ten Gauss.

In addition, it is experimentally confirmed that the variation in a vertical component of the floating flux 15 depends greatly on the speed of the thin steel strip 10. FIG. 43 shows the relationship between the output voltage and the speed of the thin steel strip 10, in the case where the vertical floating magnetic flux which is the flux outside the thin steel strip 10 in the defect-free portion was measured with the sensitivity of the magnetic sensors 7a lowered intentionally. As shown in FIG. 43, the output voltage rises as the speed of the thin steel strip 10 increases. Accordingly, the variation in vertical component of the floating magnetic flux 15 rises in accordance with the increase in speed.

Since the floating magnetic flux 15 is always generated, the leakage magnetic flux due to a defect is superimposed on the floating magnetic flux, when the defect is present on the thin steel strip 10. In addition, the floating magnetic flux is greater than the leakage magnetic flux. Each magnetic sensor 7a detects the floating flux, as shown in FIG. 42, and the leakage flux, simultaneously.

The same phenomenon occurs in the case where the magnetic sensor 7a is situated on the magnetic pole side of the thin steel strip 10, as indicated by a solid line in FIG. 42, and in the case where the magnetic sensor 7a is situated on that side of the strip 10 opposite to the magnetic poles 4a and 4b, as indicated by a broken line.

On the other hand, in order to detect the defect of the thin steel strip 10 with high precision, it is necessary to increase the sensitivity of the magnetic sensors 7a. However, as stated above, the variation component of the leakage magnetic flux due to the defect is superimposed on the high-level floating flux in the defect-free portion. Thus, if the high-sensitivity magnetic sensor array 7 is used, the magnetic sensors are saturated by the floating flux because of their narrow dynamic range, and the leakage magnetic flux due to the defect cannot be detected with high precision.

DISCLOSURE OF THE INVENTION

A first object of the invention is to provide a magnetic inspection method and apparatus capable of remarkably decreasing a floating magnetic flux intersecting a magnetic sensor for detecting a leakage magnetic flux due to a defect, and capable of preventing saturation of output of the magnetic sensor, exactly detecting a small defect, and enhancing inspection accuracy greatly.

A second object of the invention is to provide an optimal shield shape for a magnetic sensor, thus attaining a high S/N in an output signal from the magnetic sensor.

A third object of the invention is to provide a magnetic inspection apparatus capable of eliminating a noise component contained in an output signal from a magnetic sensor, which is due to a local variation in magnetic permeability of an object to be inspected, thereby remarkably enhancing the inspection accuracy of the defect.

In order to achieve the first object, in the magnetic inspection method and apparatus of this invention, a magnetic sensor for detecting a leakage magnetic flux due to an internal or surface defect of the to-be-inspected object is provided at a substantially middle point of a line connecting a pair of magnetic poles of a magnetizer for generating a magnetic field in the object or a line parallel to this connecting line. A shield body with a low coercive force is provided on each side of the magnetic sensor, which face the magnetic poles of the magnetizer.

Consideration will now be given to a magnetic path and magnetic force lines produced by the magnetizer having the pair of magnetic poles and the object situated to face the magnetic poles.

Referring to FIG. 5, magnetic poles 41a and 41b of a magnetizer faces a to-be-inspected object 42 formed of, e.g. a thin steel strip. A magnetic sensor 71a is provided at the center of a line connecting the magnetic poles 41a and 41b. A first shield body 43a is situated on one side of the magnetic sensor 71a, which faces the magnetic pole 41a. A second shield body 43b is situated on the other side of the magnetic sensor 71a, which faces the other magnetic pole 41b.

In this state, when a magnetic field generated by the magnetizer is small, magnetic force lines coming out of the magnetic pole 41a pass through a magnetic gap, enter the object 42, pass through the object 42 and an opposite magnetic gap, and enter the opposite magnetic pole 41b. When the magnetic field generated by the magnetizer is increased, the object 42 is magnetically saturated and the magnetic resistance increases. Thus, as shown in the figure, a great deal of floating magnetic flux occurs.

However, since the shield bodies with low coercive force are provided on both sides of the magnetic sensor 71a, the floating magnetic flux crossing the magnetic sensor 71a is remarkably reduced. The magnetic sensor 71a faces the object 42. Thus, if the object 42 has a defect at a location facing the magnetic sensor 71a, the sensor 71a detects a leakage magnetic flux corresponding to the defect. In this case, since the ambient floating magnetic flux 15a is small, the magnetic sensor is not saturated and only the leakage magnetic flux can efficiently be detected.

The detection of the vertical component of the leakage magnetic flux by means of the magnetic sensor 71a will now be described with reference to FIG. 6.

If a defect 44 is present in the object 42, a magnetic field 45 generated around the defect 44 exhibits a magnetic flux distribution characteristic of a very small magnetic pole, as shown in the figure. When the object 42 runs in the direction a and the defect 44 is moved to a location just below the magnetic sensor 71a, the magnetic sensor 71a detects a magnetic flux distributed vertically, as indicated by a solid line 46.

The width Wh of the magnetic field 45 due to the defect 44 is only several mm. Even if the shield bodies 43a and 43b are provided, the magnetic field 45 can be put between the shield bodies 43a and 43b. Thus, the magnetic sensor 71a can detect the leakage magnetic flux of the magnetic field 45 due to the defect 44, without being influenced by the shield bodies 43a and 43b. That is, the defect 44 can be detected with a high S/N.

In order to achieve the second object, in the magnetic inspection apparatus of the present invention, the distance between the shield bodies is set to be at least 2.2 times, and less than or equal to 2.8 times the distance between the magnetic sensor and the object.

In addition, each shield body has an L-cross section, as shown, for example, in FIGS. 9 and 25, composed of a vertical portion and a horizontal portion, and the width of the horizontal portion in the direction of arrangement of the magnetic poles is at least 0.4 times, and less than or equal to 0.6 times the distance between the magnetic poles.

When the distance A between the magnetic sensor and the shield body is too large, the ratio of a component of the floating magnetic flux in a defect-free portion, which is not shielded by the shield body and reaches the magnetic sensor, increases. If the distance A between the magnetic sensor and the shield body is decreased, the ratio of the component of the floating magnetic flux, which reaches the magnetic sensor, decreases. However, if the distance A becomes too small, the leakage magnetic flux due to the defect does not easily reach the magnetic sensor. On the other hand, the ratio of the component of the magnetic flux, which reaches the magnetic sensor, depends largely on the lift-off L represented by the distance between the magnetic sensor and the object.

Accordingly, in this invention, the relationship between the distance 2A between the shield bodies and the lift-off L is defined by $$2.2 \leq 2A/L \leq 2.8 \tag{1}$$

Thereby, the ratio of the leakage magnetic flux to the floating magnetic flux in the magnetic flux crossing the magnetic sensor can be increased, and the leakage magnetic flux can efficiently be detected. The value of formula (1) was calculated on the basis of the result of a computer simulation conducted on the magnetic field at the position of the magnetic sensor, by making and using a test model.

The relationship between the width W of the horizontal portion of each L-cross sectional shield body and the inter-magnetic pole distance B of the magnetizer will now be described.

Specifically, the floating magnetic flux and leakage magnetic flux reaching the magnetic sensor are attenuated by the presence of the shield bodies. If the ratio (W/B) of the width W of each shield body to the inter-magnetic pole distance B is varied, the attenuation amount varies. The attenuation amount differs between the floating magnetic flux and the leakage magnetic flux. Accordingly, a range in which the attenuation amount of the floating magnetic flux is large and the attenuation amount of the leakage magnetic flux is small is found. In this invention, the ratio (W/B) is defined by $$0.4 \leq W/B \leq 0.6 \tag{2}$$

Thereby, the ratio of the leakage magnetic flux to the floating magnetic flux in the magnetic flux crossing the magnetic sensor can be increased, and the leakage magnetic flux can efficiently be detected.

In order to achieve the third object, in the magnetic inspection apparatus of the present invention, a plurality of magnetic sensors are arranged at regular intervals in the width direction of the running object. A difference signal between output signals from those ones of said magnetic sensors which are separated by a predetermined distance is calculated by a corresponding subtraction circuit. An absolute value of each difference signal output from each subtraction circuit is calculated by a corresponding absolute value circuit. An arithmetic operation circuit evaluates the defect of the object on the basis of the output signal from each absolute value circuit.

For example, in the case of the object of a thin steel strip, etc., local non-uniformity in magnetic permeability occurs in the to-be-inspected body due to internal stress, non-uniformity in material quality, a variation in thickness of the object, etc. caused at the time of processing the steel strip. Accordingly, a variation component of leakage magnetic flux due to non-uniform magnetic permeability is included as noise in the detection signal of the magnetic sensor, even if the defect is not present.

In general, an area of non-uniformity of magnetic permeability is much greater than an area of a defect. Thus, the variation component of the leakage magnetic flux due to non-uniform magnetic permeability is detected simultaneously by a number of adjacent magnetic sensors. On the other hand, the leakage magnetic flux due to the defect is detected by a small number of magnetic sensors, e.g. one or two sensors. Thus, if a difference signal representing a difference between the output signals from the magnetic sensors separated by a predetermined distance is obtained, a noise component due to non-uniform magnetic permeability can be removed from the difference signal. Therefore, the S/N of the output signal of the magnetic sensor is improved.

BEST MODE OF CARRYING OUT OF THE INVENTION

An embodiment of the present invention will now be described with reference to the accompanying drawings.

Figure 1:
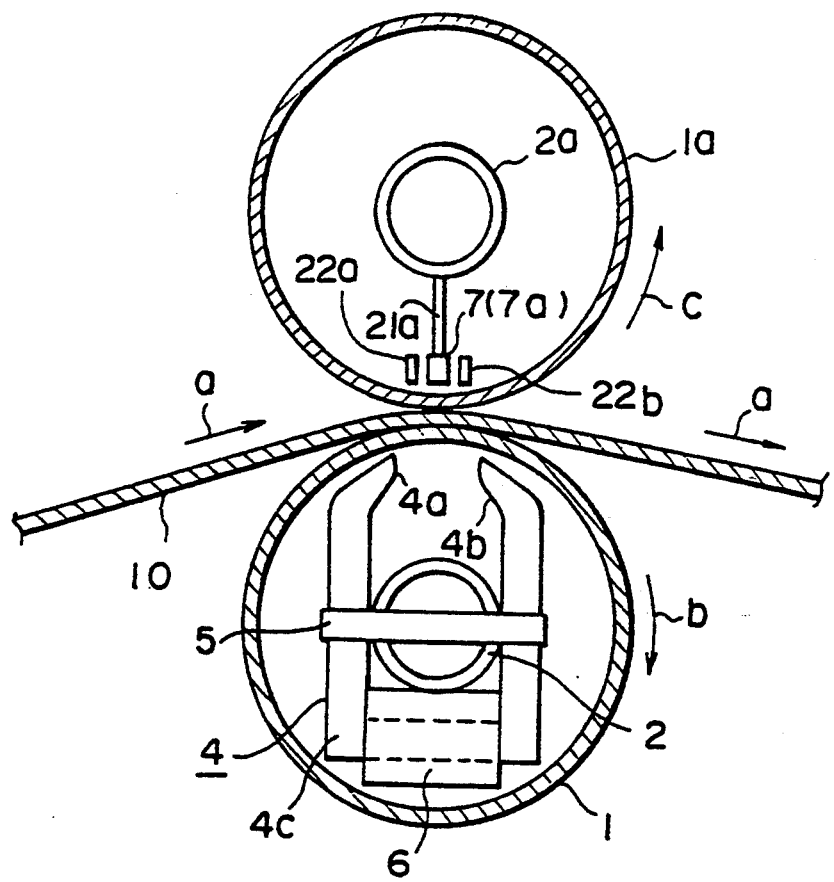
FIG. 1 is a cross-sectional view showing a magnetic inspection apparatus according to an embodiment of the present invention, taken along a plane parallel to the direction in which a thin steel strip runs.
Figure 2:
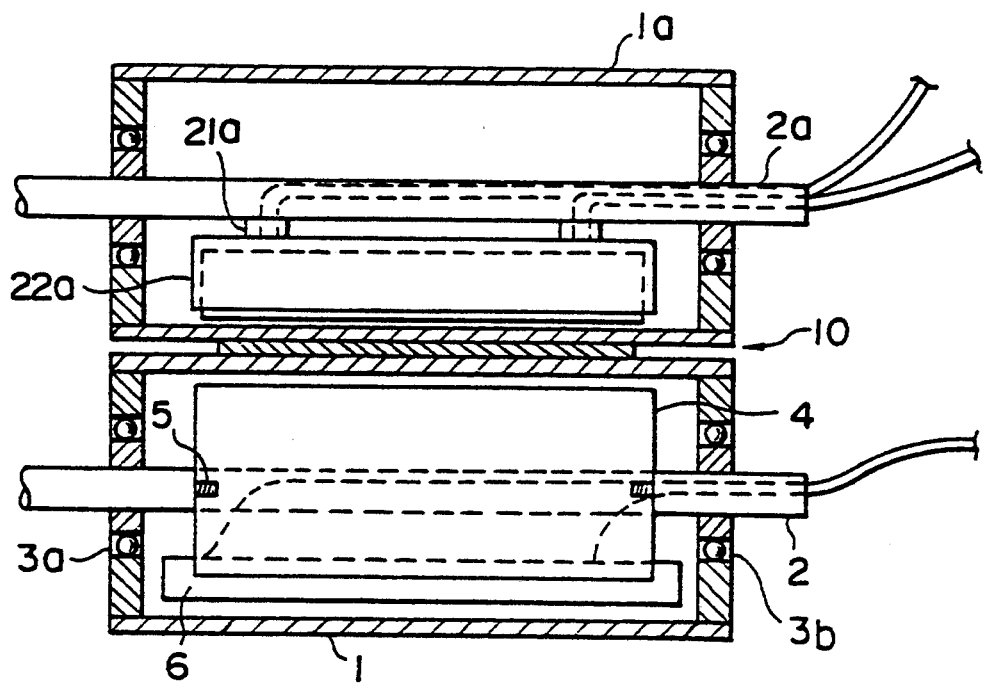
FIG. 2 is a cross-sectional view showing the apparatus, taken along a plane perpendicular to the direction in which the thin steel strip runs.
Figure 3:
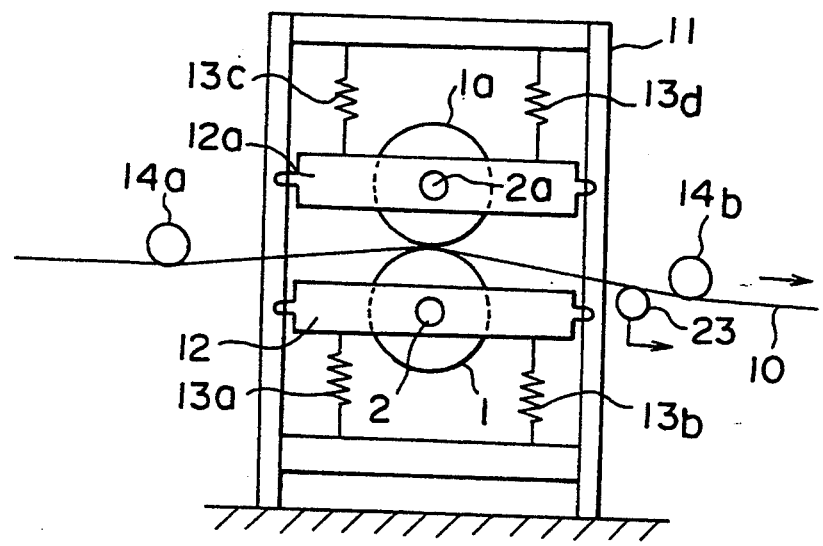
FIG. 3 is a side view showing the apparatus as built in a support apparatus.
Figure 39:
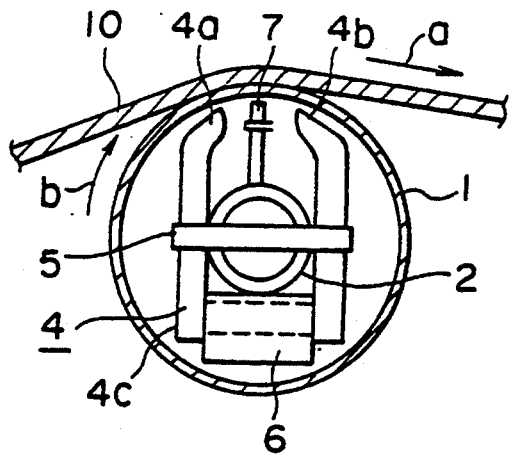
FIG. 39 is a cross-sectional view showing a conventional magnetic inspection apparatus, taken along a plane parallel to the direction in which a thin steel strip runs.
Figure 40:
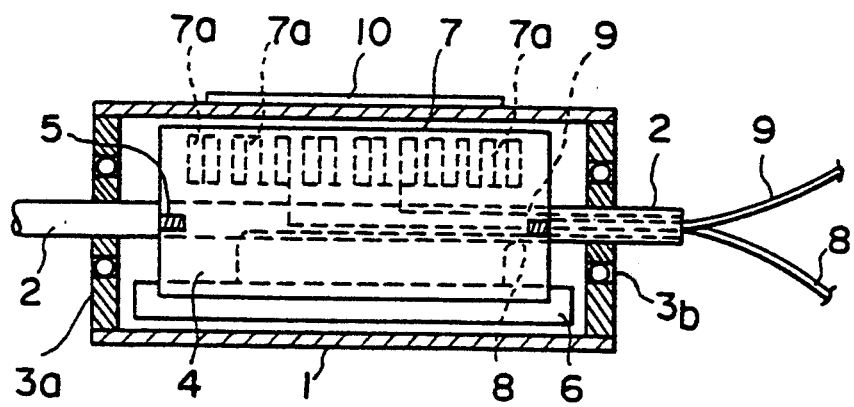
FIG. 40 is a cross-sectional view showing the conventional apparatus, taken along a plane perpendicular to the direction in which the thin steel strip runs.
Figure 41:
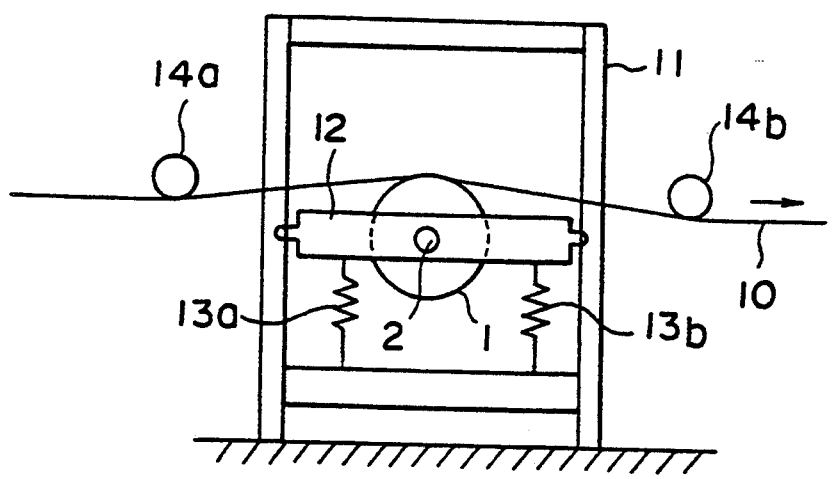
FIG. 41 is a side view showing the apparatus as built in a support apparatus.
Figure 42:
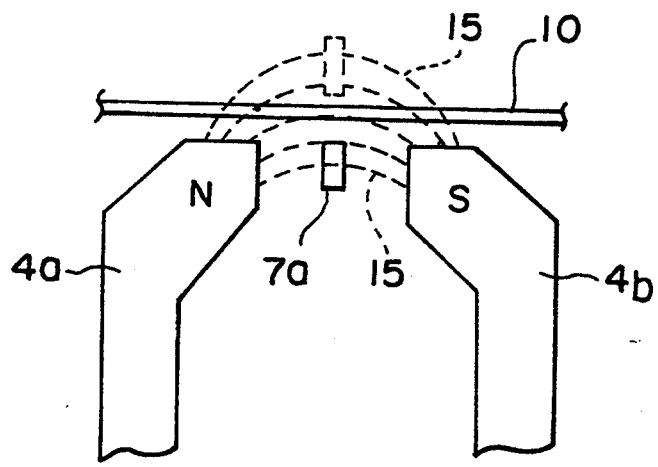
FIG. 42 is a diagram for illustrating the problem in the conventional apparatus.

FIGS. 1, 2 and 3 are cross-sectional views showing a magnetic inspection apparatus according to the embodiment which is incorporated in an inspection line in a factory. The same parts as in the conventional magnetic inspection apparatus shown in FIGS. 39, 40 and 41 are denoted by like reference numerals. Thus, detailed descriptions of the common parts are omitted.

In this embodiment, a thin steel strip 10 or an object to be inspected is interposed between upper and lower hollow rolls 1a and 1a. In FIG. 3, two horizontal arms 12 and 12a are supported within a frame 11 by means of spring members 13a, 13b, 13c and 13d. Thus, the horizontal arms 12 and 12a are vertically movable. Stationary shafts 2 and 2a of the magnetic inspection apparatus are fixed at middle parts of the horizontal arms 12 and 12a. A pair of guide rolls 14a and 14b for guiding the thin steel strip 10 between the hollow rolls 1 and 1a of the magnetic inspection apparatus are provided on both sides of the frame 11.

In FIGS. 1 and 2, an end portion of the stationary shaft 2 penetrates a center shaft of the lower hollow roll 1 made of a non-magnetic material. The stationary shaft 2 is rotatably supported by a pair of rolling bearings 3a and 3b such that the shaft 2 is situated along the center axis of the hollow roll 1. Thus, the hollow roll 1 is freely rotatable about the stationary shaft 2.

Within the hollow roll 1, a magnetizing core 4c around which a magnetizing coil 6 of a magnetizer 4 is wound is fixed to the stationary shaft 2 via a support member 5, such that magnetic poles 4a and 4b are situated close to the inner peripheral surface of the hollow roll 1.

On the other hand, the upper hollow roll 1a, which is provided above the lower hollow roll 1 with the thin steel strip 10 interposed, is rotatable about a stationary shaft 2a. When the thin steel strip 10 runs in the direction a, the roll 1a rotates in the direction c. A magnetic sensor array 7 is fixed to the stationary shaft 2a of the hollow roll 1a via a support rod 21a so as to face the magnetic poles 4a and 4b of the magnetizer 4 housed in the lower hollow roll 1. The magnetic sensor array 7 comprises magnetic sensors 7a arranged linearly in the width direction of the thin steel strip 10. Signal cables of the magnetic sensors 7a are led out through the stationary shaft 2a.

One shield plate 22a is situated on one side of the magnetic sensor array 7 so as to face the magnetic pole 4a. Similarly, the other shield plate 22b is situated on the other side of the sensor array 7 so as to face the magnetic pole 4b. The shield plates 22a and 22b are made of a material having high magnetic permeability and low coercive force. In this embodiment, the shield plates 22a and 22b are made of Permalloy. The shield plates 22a and 22b are fixed to the center shaft 2a by means of support members (not shown).

Figure 4:
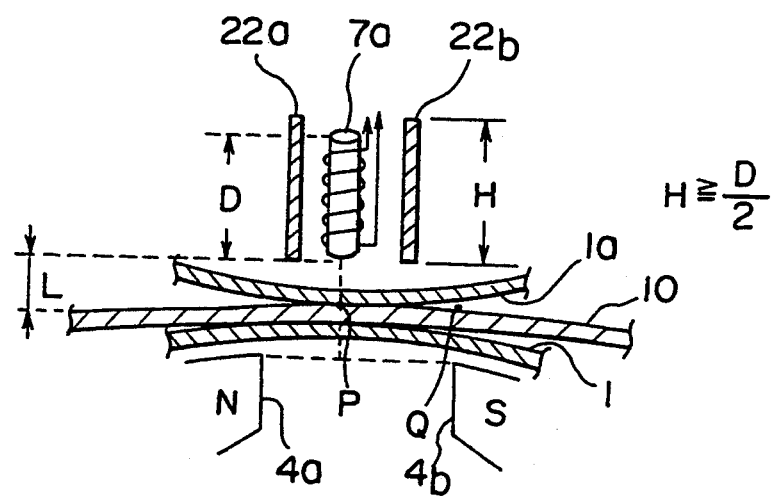
FIG. 4 is a partly enlarged view showing an important portion of the apparatus.
Figure 5:
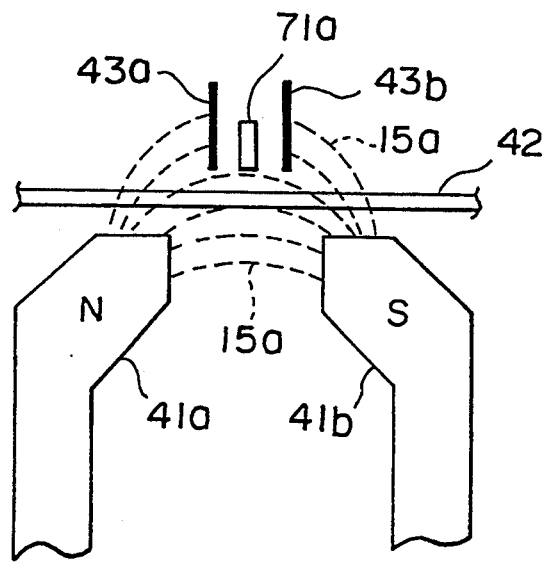
FIG. 5 is a schematic diagram for illustrating the operational principle of the present invention.
Figure 6:
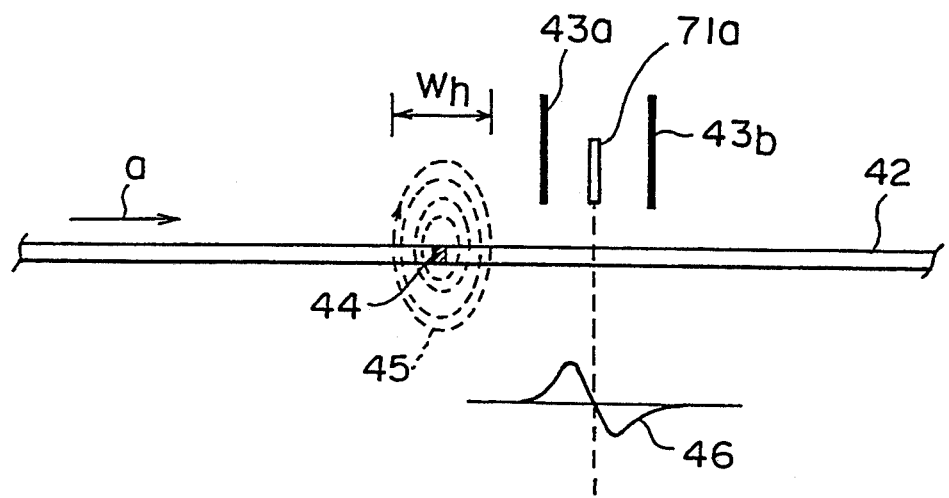
FIG. 6 shows the positional relationship between a leakage flux and shield bodies, for illustrating the operational principle of the invention.

FIG. 4 is an enlarged view of an important portion. Each magnetic sensor 7a of the magnetic sensor array 7 is a saturable-type magnetic sensor formed by winding a detection coil around a rod-shaped core of ferromagnetic material. The height H of each shield plate 22a, 22b is greater than the length D of the rod-shaped core of each magnetic sensor 7a. The lower ends of the shield plates are substantially on a level with the lower end of each magnetic sensor 7a. It suffices if the height H is at least ½ of the length D of the rod-shaped core.

In this embodiment, the length D of each magnetic sensor 7a is 5 mm. The height H of each shield plate 22a, 22b is 16 mm, and the thickness of each shield plate is 0.2 mm. Each shield plate 22a, 22b is separated from the center axis of each magnetic sensor 7a by 4 mm (A=4 mm). A lift-off or a distance between each magnetic sensor 7a and each shield plate 22a, 22b, on the one hand, and the thin steel strip 10, on the other, is 3.6 mm. The length of each shield plate 22a, 22b in the width direction of the thin steel strip 10 is greater than the width (length) of the magnetic sensor array 7.

In the magnetic inspection apparatus having the above structure, when the thin steel strip 10 is traveled in the direction a while it is clamped between the hollow rolls 1 and 1a under a predetermined pressure, the hollow rolls 1 and 1a rotate in the directions b and c.

In this state, an excitation current is supplied to the magnetizing coil 6 and a closed magnetic path is formed by the running thin steel strip 10 and the magnetic poles 4a and 4b of the magnetizing core 4c stored in the lower hollow roll 1. When the thin steel strip 10 has an internal or surface defect, a leakage magnetic flux occurs. The leakage magnetic flux is detected by the magnetic sensor 7a of the sensor array 7 housed in the upper hollow roll 1a, which magnetic sensor 7a corresponds to the position of the defect. This magnetic sensor 7a outputs a detection signal.

In the above structure, the gravitational force of the thin steel strip 10 is not directly exerted on the upper hollow roll 1a. Thus, the thickness of the upper hollow roll 1a is made less than that of the lower hollow roll 1. Accordingly, the distance between the magnetic sensor array 7 and the thin steel strip 10 can be decreased, and the detection sensitivity of the sensor array 7 can be enhanced.

Figure 7:
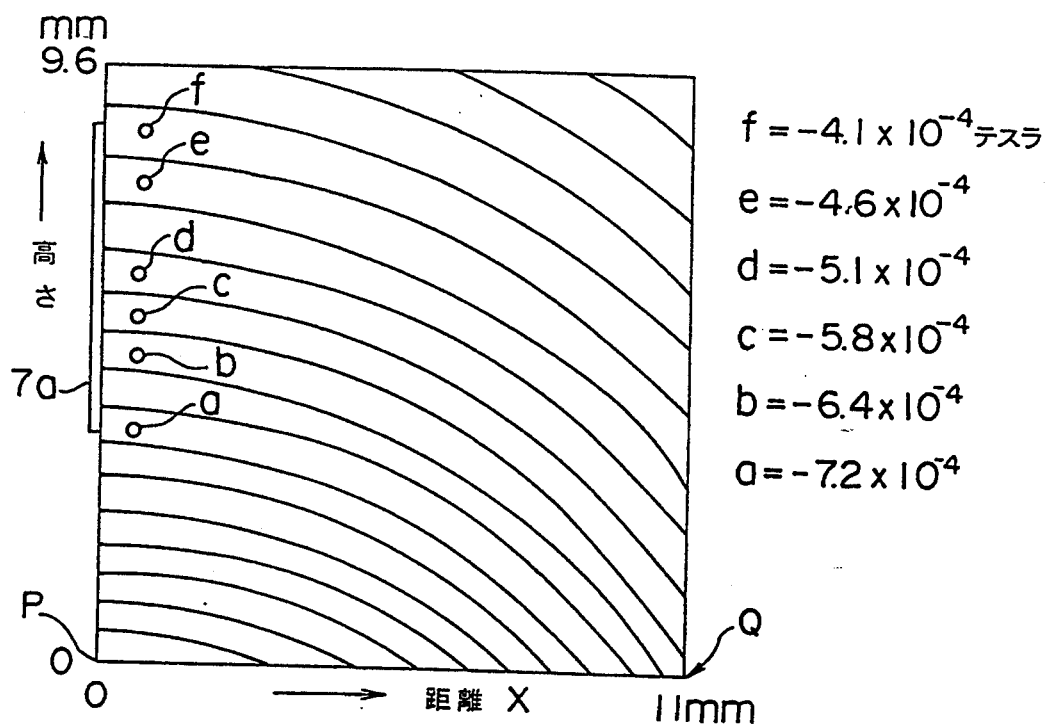
FIG. 7 shows a simulation result of a magnetic flux intensity near a magnetic sensor when the shield body of the apparatus of the embodiment is not provided.
Figure 8:
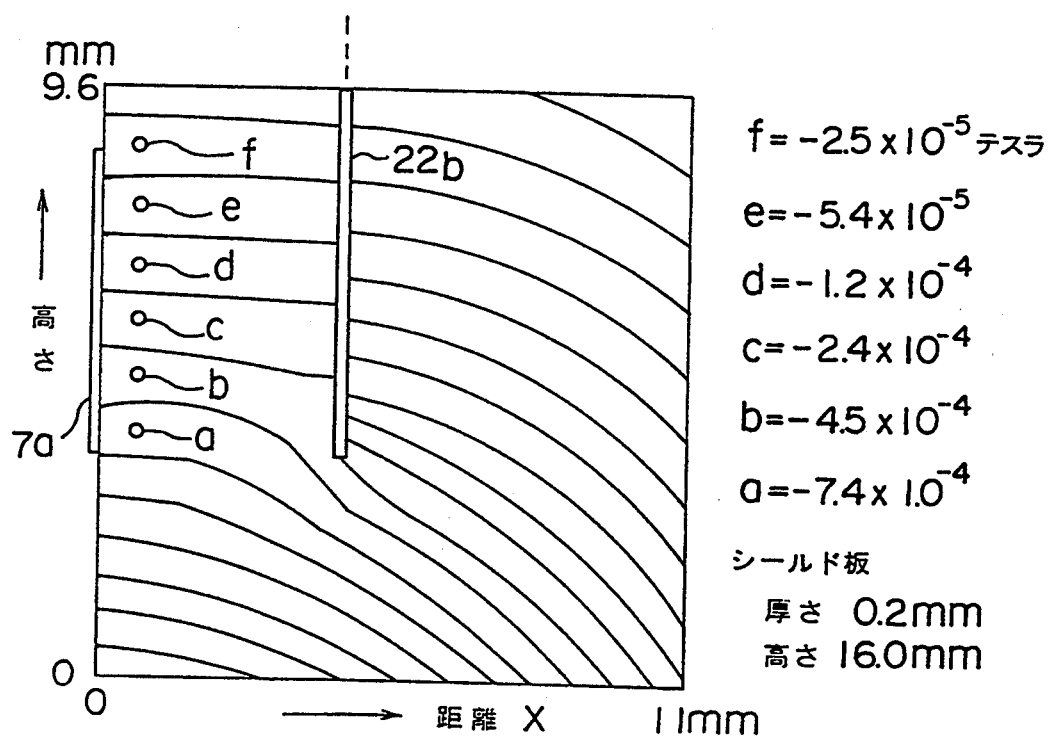
FIG. 8 shows a simulation result of a magnetic flux intensity near the magnetic sensor when the shield body of the apparatus of the embodiment is provided.

FIGS. 7 and 8 are graphs showing computer simulation results, indicating floating magnetic flux distributions obtained before and after the shield plates 22a and 22b as shown in FIG. 4 are provided. In each graph, the original point P is an intersection between the upper surface of the thin steel strip 10 (in FIG. 4) and the center line between the magnetic poles 4a and 4b. The horizontal axis indicates the horizontal distance X (unit=mm), and the right end point Q corresponds to the tip point of the magnetic pole 4b. The vertical axis indicates the vertical distance (unit=mm). Solid lines indicate magnetic force lines produced between the magnetic poles 4a and 4b.

In FIGS. 7 and 8, a, b ... f indicate vertical locations near the magnetic sensor 7a at the distance X=5 mm. The values a to f stated on the right side of each graph indicate vertical components of magnetic field (floating magnetic field) at the corresponding locations. Accordingly, the (−) signs indicate downward magnetic field.

The vertical magnetic field at the distance X=0 is symmetric and becomes 0 in the simulation result. Thus, the respective values are obtained at the distance X=1 mm.

FIG. 7 shows the case where the shield plate 22b is not provided, and FIG. 8 shows the case where the shield plate 22b is provided. As shown in the figures, when the shield plate 22b is provided, it is understood that the vertical component of the floating magnetic flux intersecting at the respective locations of the magnetic sensor 7a is remarkably reduced.

Figure 9:
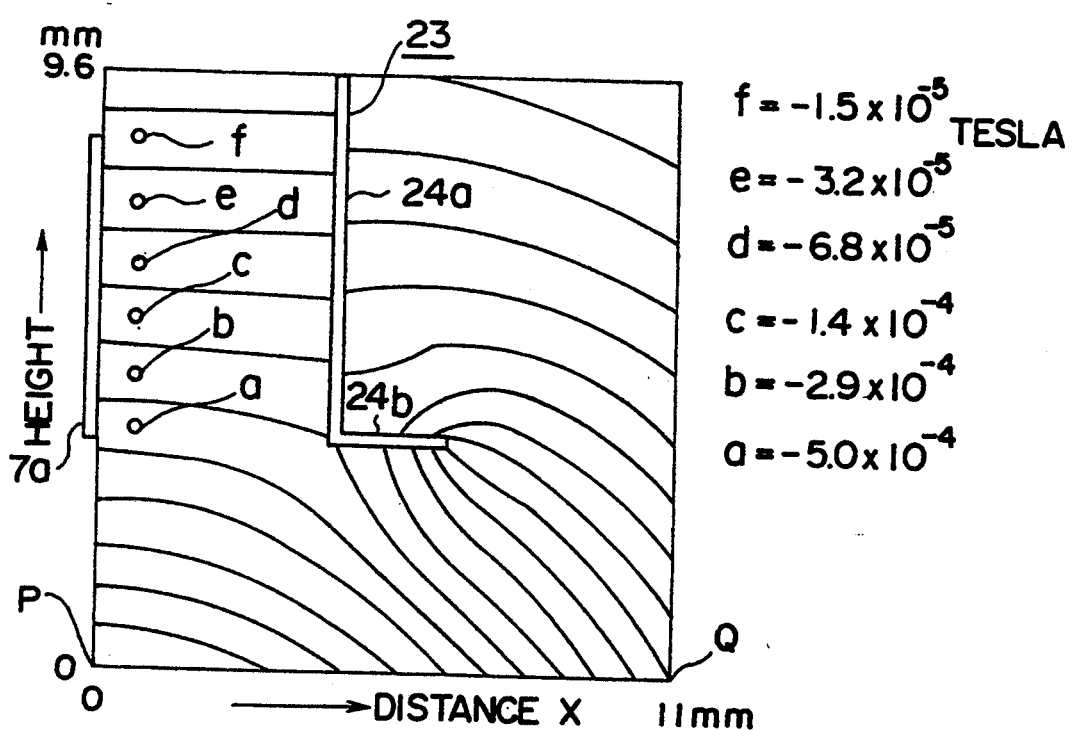
FIG. 9 shows a simulation result of the magnetic flux intensity near the magnetic sensor when the shield body of the apparatus, which has an L-cross section, is provided.

FIG. 9 shows the case where a shield plate 23 having an L-cross section was used as a shield body. As shown in FIG. 9, the shield plate 23 comprises a vertical portion 24a having the same shape as the shield plate 22b shown in FIG. 4, and a horizontal portion 24b extending outwardly from the lower end of the vertical portion 24a. The horizontal width W of the horizontal portion 24b is 2 mm.

It is suggested that by attaching the horizontal portion 24b to the lower end of the shield plate 23, the floating magnetic flux extending to the inside of the shield plate 23 from the lower end region of the plate 23 can be remarkably reduced.

Based on the above simulation results, two types of shield plates 22a, 22b and 23 were manufactured and arranged on both sides of the magnetic sensor array 7. Standard defective samples having artificial defects (through holes) of 0.2 mmΦ, 0.3 mmΦ, 0.6 mmΦ and 0.9 mmΦ were substituted for the thin steel strip 10, where Φ represents the diameter and the defects of the samples were inspected. Thus, the inspection results were obtained.

Figures 10A, 10B:
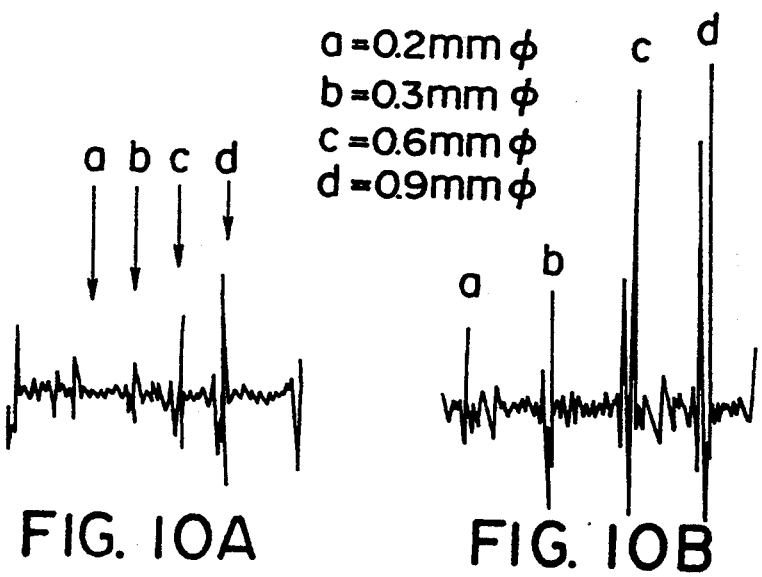
FIG. 10A shows a waveform at the time the apparatus is not provided with the shield plate.
FIG. 10B shows a waveform at the time the apparatus is provided with the shield plate.

FIG. 10A shows an output waveform of each magnetic sensor 7a where the shield plates are not provided, and FIG. 10B shows an output waveform of each magnetic sensor 7a after the shield plates 22a and 22b shown in FIG. 4 are provided. The sensitivity of the magnetic sensor 7a at the time the waveform of FIG. 10B was observed is set to be higher than the sensitivity at the time the waveform of FIG. 10A was observed.

Regarding the waveform of FIG. 10A obtained in the case where the shield plates are not provided, when the magnetizing force is increased, the magnetic sensor is saturated due to the increase in floating magnetic flux. However, if the magnetizing current is decreased, the output values (amplitudes) corresponding to the magnitude of defects of 0.2 to 0.9 mmΦ are not obtained. In addition, the S/N is low. By contrast, in the case of the waveform of FIG. 10B, the shield plates 22a and 22b are attached, and the output values (amplitudes) corresponding to the magnitude of defects are obtained and the S/N is remarkably enhanced.

Figure 11:
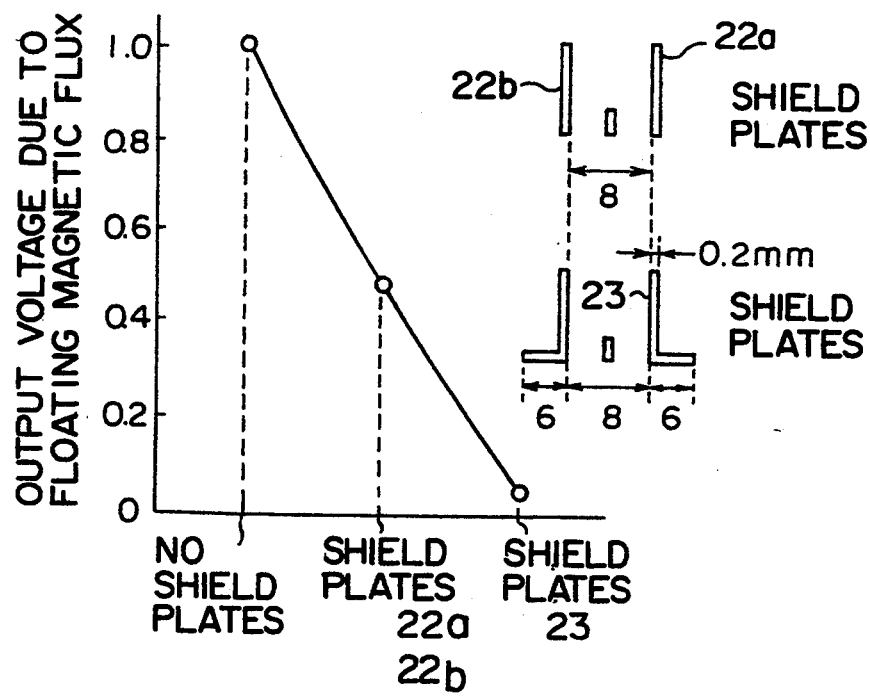
FIG. 11 shows the relationship between the floating magnetic flux and the presence/absence of the shield plates in the apparatus.

FIG. 11 shows actual measurement data on the intensity of the floating magnetic flux detected by each magnetic sensor 7a in the case where the defect-free thin steel strip 10 was inspected by the apparatus of the embodiment. The measurement was conducted under the conditions that no shield plate was provided, the shield plates 22a and 22b shown in FIG. 4 were provided, and the shield plate 23 having the L-cross section was provided.

As shown in the figure, by providing the shield plates, it is understood that the output voltage due to floating magnetic flux detected by each magnetic sensor 7a is remarkably decreased. As stated above, the leakage magnetic flux due to the defect is hardly influenced by the presence of the shield plate. As a result, the ratio of the leakage magnetic flux due to the defect to the floating magnetic flux increases, and the defect detection S/N increases.

Figure 12:
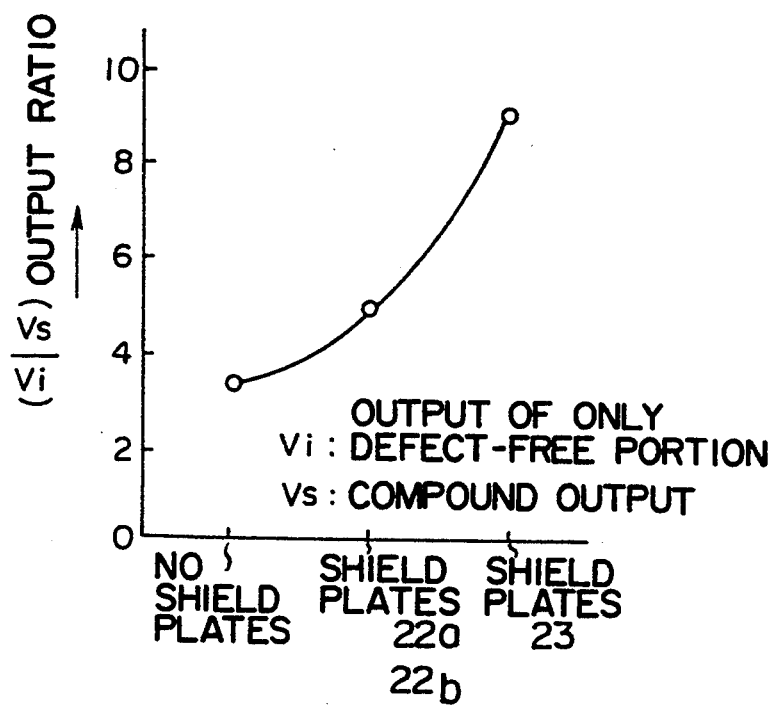
FIG. 12 shows the relationship between the magnetic sensor output and the presence/absence of the shield plates in the apparatus.

FIG. 12 is a graph showing the output ratio (Vs/Vi) between the output voltage Vi due to the floating magnetic flux of the defect-free portion and the output voltage vs obtained by compounding the leakage voltage due to a defect in the case where the defect exists and the output voltage Vi due to the floating magnetic flux.

The output ratio (Vs/Vi) was experimentally obtained under the aforementioned measurement conditions.

As can be seen from this graph, by providing the shield plate, the ratio of the output voltage due to the leakage magnetic flux contained in the entire output voltage (compound voltage Vs) of the magnetic sensor 7a increases.

It was thus proved by the measurement results shown in FIGS. 10A to 12 that the simulation results shown in FIGS. 7 to 9 are correct.

Accordingly, even if the generated magnetic field generated by the magnetizer is increased to increase the leakage magnetic flux due to the defect, most of the floating magnetic flux of the defect-free portion resulting from the increase in the magnetic field is shielded by the shield plates 22a, 22b, 23 and does not reach the magnetic sensor array 7. Accordingly, by increasing the generated magnetic field, only the leakage magnetic flux can be increased and the S/N of the output voltage due to the defect detected by each magnetic sensor 7a is remarkably increased.

Furthermore, since the output voltage is not saturated, the output voltage corresponding to the magnitude of the defect is obtained. Thus, a small defect in the thin steel strip 10 can be detected with high precision.

Figure 43:
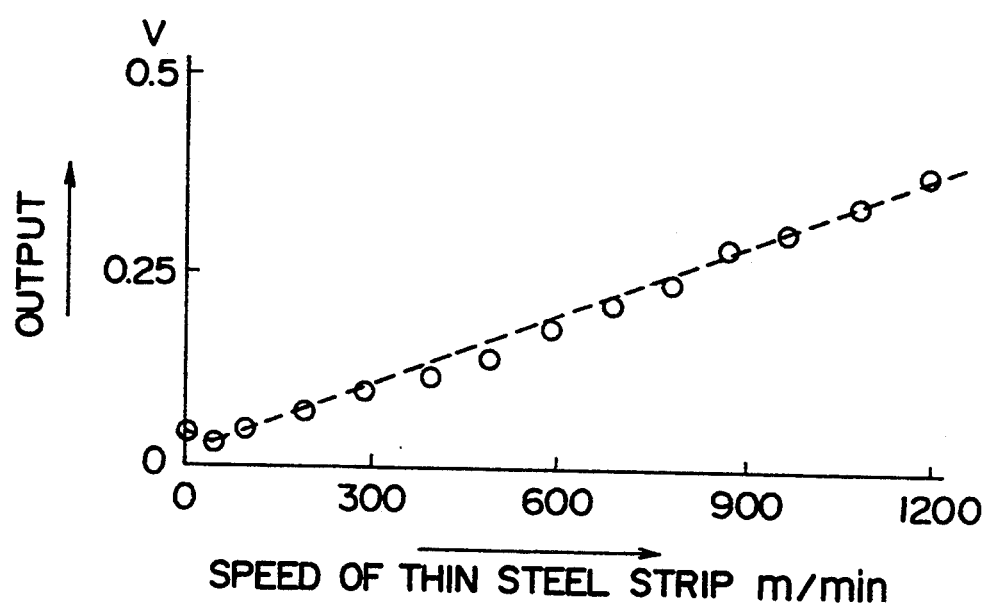
FIG. 43 shows the relationship between a vertical component of a floating magnetic flux and the speed at which the thin steel plate runs in the conventional apparatus.

Besides, when the speed at which the thin steel strip 10 is increased, the vertical component of the floating magnetic flux increases, as shown in FIG. 43. However, the floating magnetic flux itself input to each magnetic sensor 7a decreases. Thus, even if the speed of the thin steel strip 10 is increased, the S/N does not decrease in particular. Therefore, by increasing the speed of the strip 10, the inspection efficiency can be enhanced.

However, if the distance 2A between the shield plates 22a and 22b is set to be too small, not only the floating magnetic flux but also the leakage magnetic flux due to the defect in the thin steel strip 10 is shielded. As a result, the S/N of the output signal of the magnetic sensor 7a is lowered, to the contrary. Inversely, if the distance 2A between the shield plates 22a and 22b is too large, the floating magnetic flux is not shielded. Thus, an optimal value should be present with respect to the distance 2A.

Figure 13:
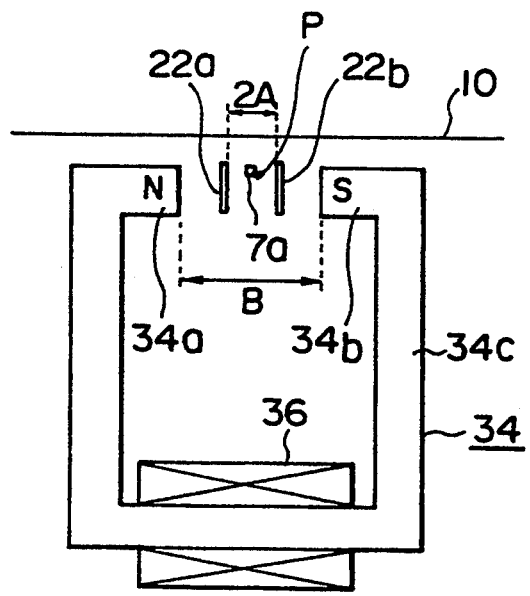
FIG. 13 shows the positional relationship between the distance between the magnetic poles of the magnetizer and the distance between the shield bodies.

Under the circumstances, the inventors experimentally produced a test model of the magnetizer 34 having the shape as shown in FIG. 13. The distance B between magnetic poles 34a and 34b is variable between 10 mm, 20 mm and 30 mm. The vertical component of the magnetic flux density detected by the magnetic sensor 7a situated at the center between the magnetic poles was calculated by the aforementioned computer simulation in the case where the distance 2A between the shields was variably changed.

It is supposed that the defect is present at the center of the thin steel strip 10. As stated above, since the vertical magnetic field on the center line between the magnetic poles cannot be calculated, the vertical component of the magnetic flux density at a point P displaced towards the magnetic pole from the center by 1 mm (X=1 mm) is calculated. And the S/N of the vertical component is calculated.

Specifically, S indicates the differential magnetic flux density between the leakage magnetic flux due to the defect and the floating magnetic flux of the defect-free portion of the thin steel strip 10, and N indicates the variation in floating magnetic flux density of the entire thin steel strip in the case where the magnetic sensor 7a oscillates in the X-direction by ±0.2 mm with respect to the point P as a central point. That is, N is noise due to the leakage magnetic flux which occurs when the magnetic sensor 7a oscillates owing to the thin steel strip 10 running on the rolls and by the rolls.

Figure 15:
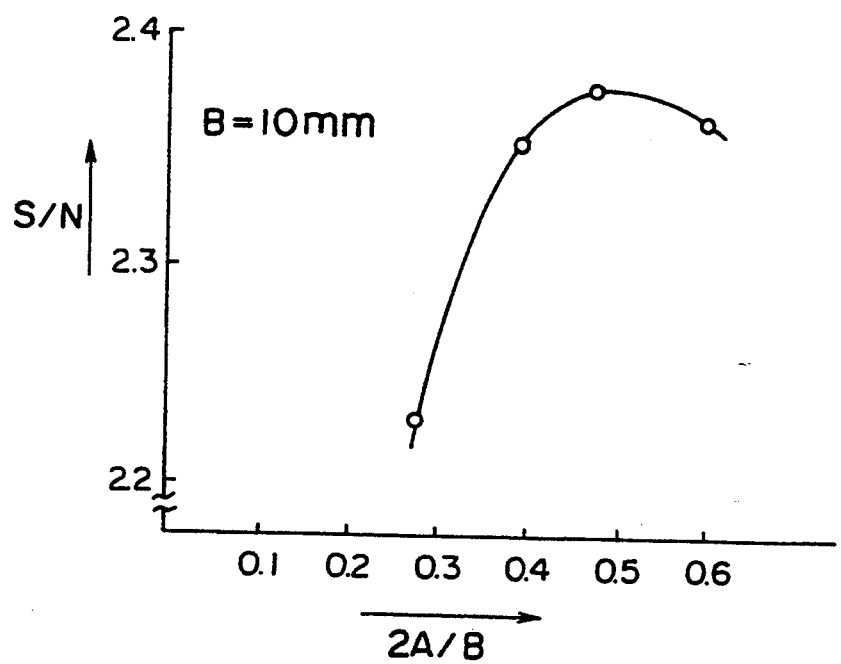
FIG. 15 shows the relationship between the shield distance of the shield shape shown in FIG. 13 and the S/N of the output signal from the magnetic sensor.

FIG. 15 is a characteristic graph showing the variation in the S/N of the vertical component at point P in the case where the distance 2A between the shield plates is varied in the state in which the inter-magnetic pole distance B of the magnetizer 34 is set at 10 mm. The horizontal axis or abscissa is set at the value (2A/B) obtained by normalizing the inter-shield plate distance 2A by the inter-magnetic pole distance B.

As can be seen from FIG. 15, in the case where the inter-magnetic pole distance B is 10 mm, the S/N takes a maximal value when the inter-shield plate distance 2A normalized by the distance B is about 0.5.

Figure 16:
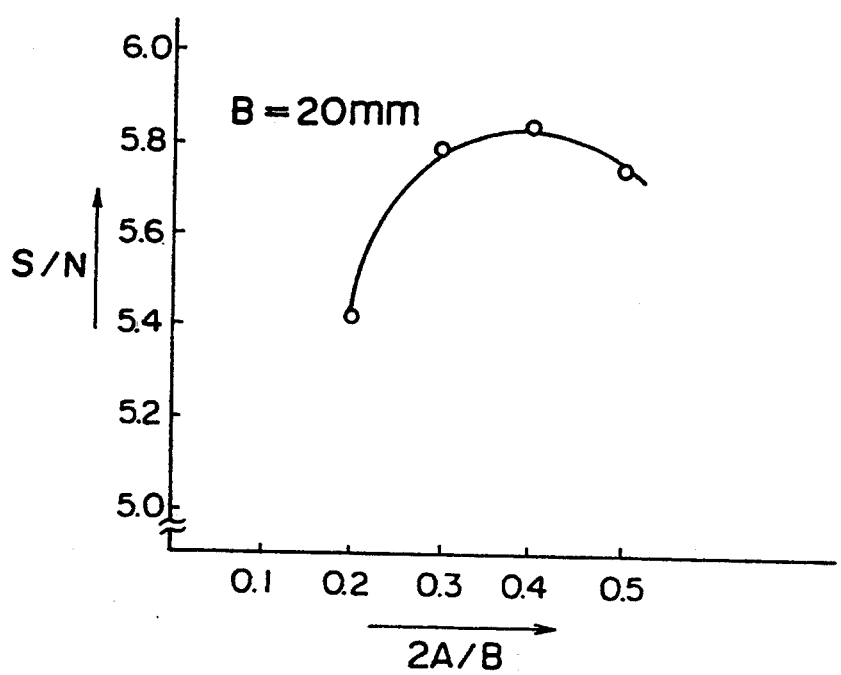
FIG. 16 shows the relationship between the shield distance of the shield shape shown in FIG. 13 and the S/N of the output signal from the magnetic sensor.

FIG. 16 is a characteristic graph showing the variation in the S/N in the case where the distance B is 20 mm. In the case where the inter-magnetic pole distance B is 20 mm, the S/N takes a maximal value when the normalized inter-shield plate distance (2A/B) is about 0.4.

Figure 17:
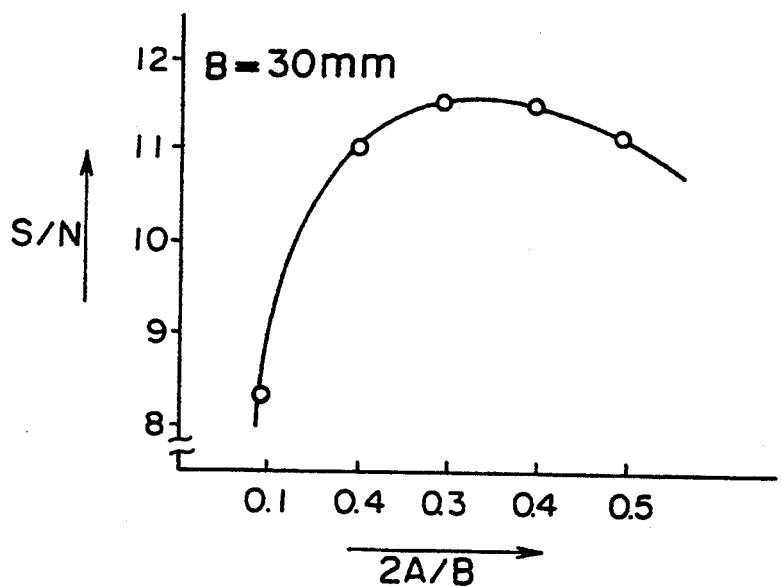
FIG. 17 shows the relationship between the shield distance of the shield shape shown in FIG. 13 and the S/N of the output signal from the magnetic sensor.

Similarly, FIG. 17 is a characteristic graph showing the variation in the S/N in the case where the inter-magnetic pole distance B is 30 mm. In the case where the distance B is 30 mm, the S/N takes a maximal value when the normalized inter-shield plate distance (2A/B) is about 0.3.

Figure 18:
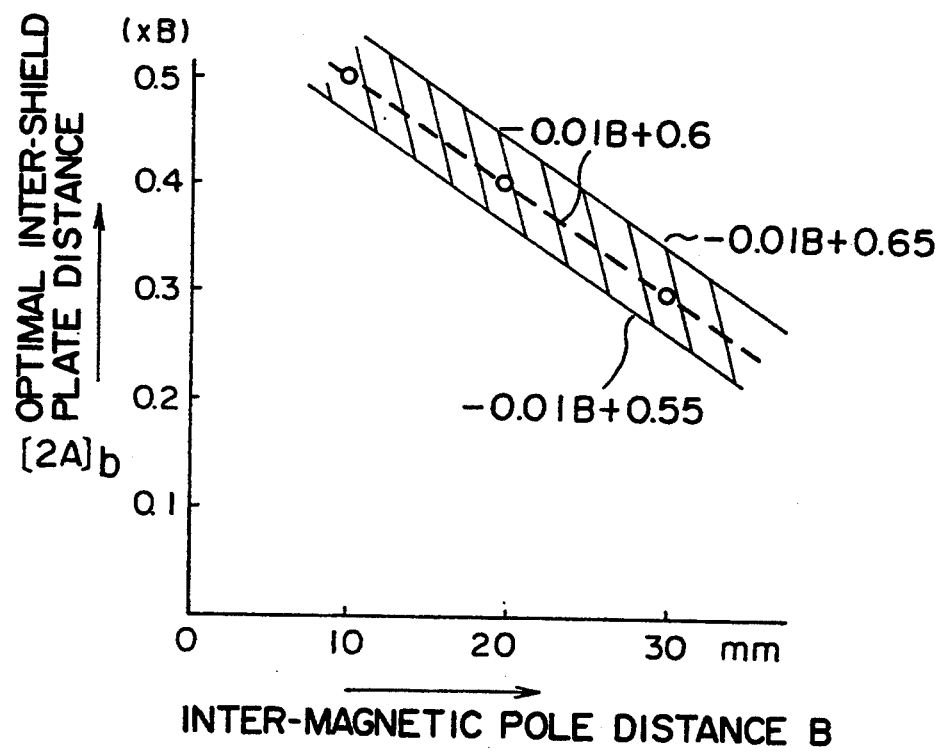
FIG. 18 shows the relationship between the inter-magnetic pole distance of the shield shape shown in FIG. 13 and the optimal shield distance.

Referring to FIGS. 15, 16 and 17, it is assumed that there is a optimal inter-shield plate distance [2A]b. FIG. 18 is a graph showing the relationship between the inter-magnetic pole distance B and the inter-shield plate distance 2A at which the maximal S/N is obtained when the distance B is 10 mm, 20 mm and 30 mm, i.e. the optimal inter-shield plate distance [2A]b. The optimal inter-shield plate distance [2A]b and the inter-magnetic pole distance B meet the relationship of equation (3):

$$[2A]b = -0.01B + 0.6 \tag{3}$$

wherein the unit of 2A and B is mm.

Accordingly, if the inter-shield plate distance [2A] is set to meet equation (3) in relation to the inter-magnetic pole distance B, the optimal S/N is obtained. In the actual apparatus, if the distance [2A] meets formula (4), a practically sufficiently high S/N is obtained:

$$-0.01B + 0.55 \leq 2A \leq -0.01B + 0.65 \tag{4}$$

The shape of the shield body provided on that side of the magnetic sensor 7a which faces the magnetic pole 4a, 4b will now be considered.

Figure 14:
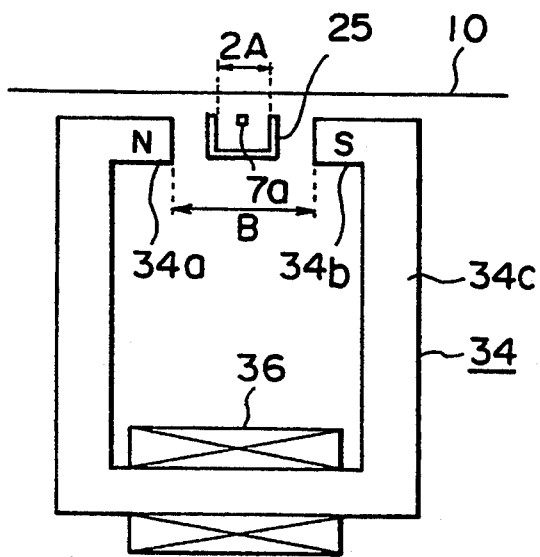
FIG. 14 shows the relationship between the distance between the magnetic poles of the magnetizer and the shape of the shield body.

Possible shapes of the shield body are a pair of shield plates 22a, 22b shown in FIG. 13, shield plate 23 having the L-cross section shown in FIG. 9, and a shield body 25 having a U-cross section as shown in FIG. 14. Specifically, the shield body 25 can magnetically shield not only the sides of the magnetic sensor 7a but also that face of the sensor 7a which is not opposed to the thin steel strip 10. Accordingly, a floating magnetic flux parallel to the thin steel strip 10 enters one of the vertical portions of the magnetic shield body 25, passing through an intermediate horizontal portion and goes out of the other vertical portion. As a result, it becomes difficult for the floating magnetic flux to enter the inside of the shield body 25 having the U-cross section. Thus, the S/N of the output signal of the magnetic sensor 7a is further enhanced.

Suppose that the distance between the vertical portions of the shield body 25 is 2A, like the distance between the shield plates 22a and 22b shown in FIG. 13.

Using the shield body 25 with the U-cross section, the relationship between the optimal distance [2A]b and the inter-magnetic pole distance B for obtaining the optimal S/N was examined by the same method as with the shield plates 22a and 22b shown in FIG. 13. Like the [S/N]22 of the optimal shield distance [2A]b of the shield plates 22a and 22b shown in FIG. 13, [S/N]25 of the optimal distance [2A]b of the shield body 25 shown in FIG. 14 was obtained with respect to each inter-magnetic pole distance B.

Figure 19:
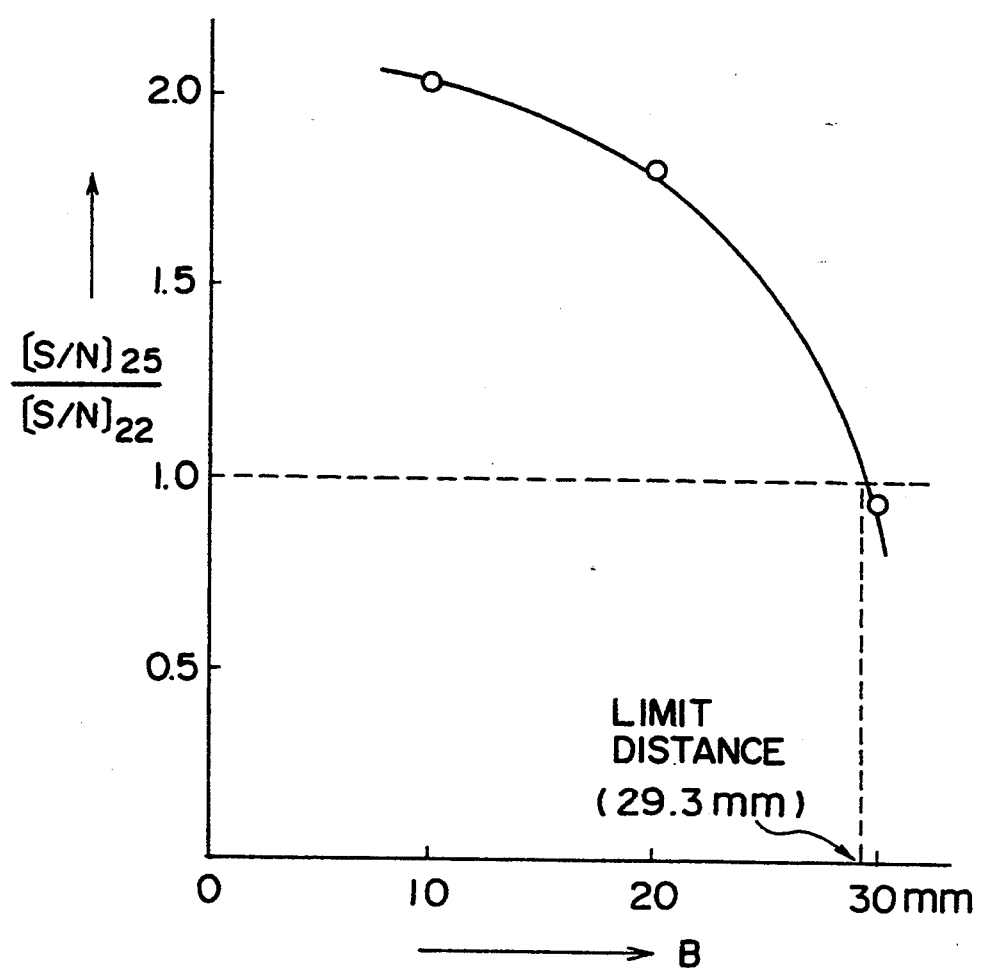
FIG. 19 shows the relationship between the inter-magnetic pole distance of the shield shape shown in FIG. 14 and the S/N of the output signal from the magnetic sensor in a different shield mode.

For each inter-magnetic pole distance B, the ratio [S/N]25/[S/N]22 of the optimal [S/N]25 of the shield body 25 to the optimal [S/N] of the shield plates 22a and 22b was calculated. FIG. 19 is a graph showing the calculation result. As can be seen from the characteristic graph of FIG. 19, when the inter-magnetic pole distance B is less than a limit distance of 29.3 mm, a higher S/N is obtained with the shield body 25 having the U-cross section shown in FIG. 14. Inversely, when the distance B exceeds 29.3 mm, a higher S/N is obtained with the shield plates 22a and 22b arranged in parallel as shown in FIG. 13.

The reason why the inversion phenomenon of the S/N characteristic occurs at a specific value of the inter-magnetic pole distance B is as follows.

When the distance B is less than 29.3 mm, the floating magnetic flux parallel to the thin steel strip 10 is greatly attenuated while passing through the horizontal portion of the shield body 25 with the U-cross section. However, when the distance B exceeds 29.3 mm, the magnetic flux extending normally towards the thin steel plate 10 is biased to the shield body 25. Consequently, the floating magnetic flux of the sensor unit increases, and the S/N decreases.

Accordingly, the limit distance 29.3 mm is definitely determined when the width 2A of the shield plates 22a and 22b, or shield body 25, in the direction of arrangement of the magnetic poles and the inter-magnetic pole distance B meet the condition of equation (3).

Figure 20:
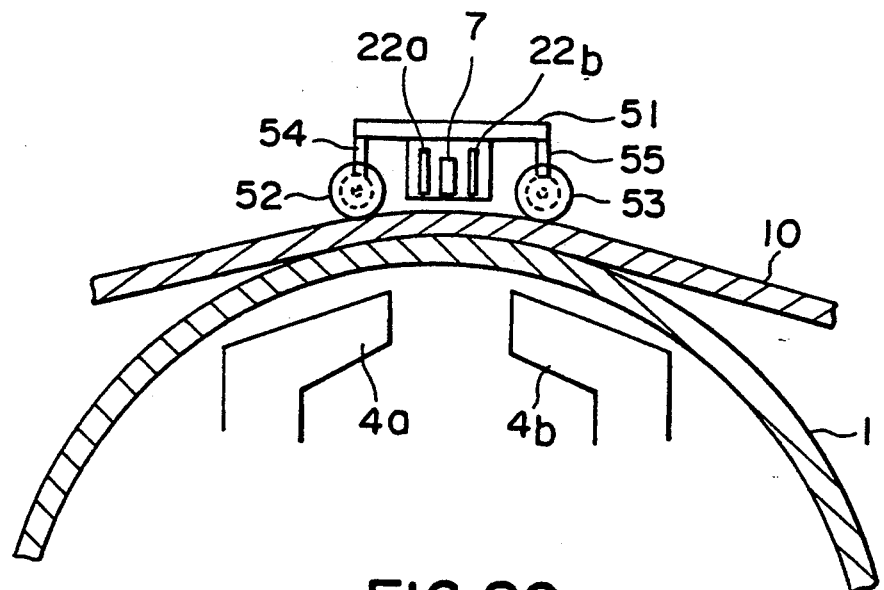
FIG. 20 shows a cross-sectional view showing a schematic structure of a magnetic inspection apparatus according to another embodiment of the invention.
Figure 21:
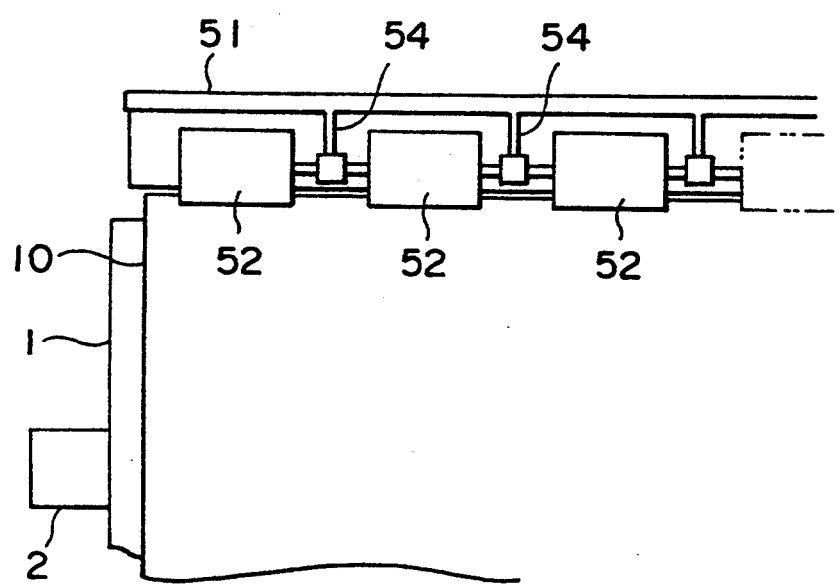
FIG. 21 is a front view of an important portion of the apparatus.

FIG. 20 is a cross-sectional side view showing an important portion of a magnetic inspection apparatus according to another embodiment of the present invention, and FIG. 21 is a front view of the important portion of this apparatus. The same parts as in the embodiment of FIG. 1 are denoted by like reference numerals. Thus, detailed descriptions of the common parts are omitted.

The magnetic sensor array 7 arranged along the center axis between the magnetic poles 4a and 4b housed within the hollow roll 1 and the shield plates 22a and 22b provided on both sides of the magnetic sensor array 7 are attached to a support frame 51 situated along the axis of the hollow roll 1. The support frame 51 is supported on the upper surface of the thin steel plate 10 by means of a number of rollers 52 and 53 arranged in two lines along the axis of the hollow roll 1 via support arms 54 and 55.

Thus, the lift-off L (or the distance) between the magnetic sensors 7a of the magnetic sensor array 7 and the surface of the thin steel strip 10 is kept at a constant value determined by the outside diameter of each roller 52, 53 and the shape of the support frame 51. The horizontal movement of the support frame 51 is restricted by a support mechanism (not shown) so as to keep a predetermined relationship between the magnetic sensors 7a and the magnetic poles 4a and 4b.

According to this magnetic inspection apparatus with this structure, the outside diameter of each roller 52, 53 is much smaller than that of the hollow roll 1a shown in FIG. 1. Thus, the moment of inertia of each roller 52, 53 is much smaller than that of the hollow roll 1a shown in FIG. 1. Therefore, it is not necessary to increase the strength of the support frame 51 and rollers 52 and 53 in particular.

In addition, the maintenance of the magnetic sensor array 7 is easier than in the case where the array 7 is housed within the hollow roll 1a.

Figure 22A:
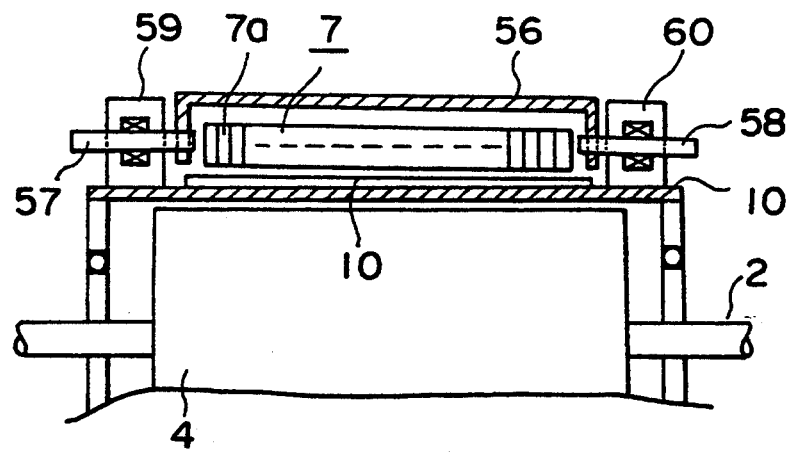
FIG. 22A is a cross-sectional view showing a schematic structure of a magnetic inspection apparatus according to still another embodiment of the invention.
Figure 22B:
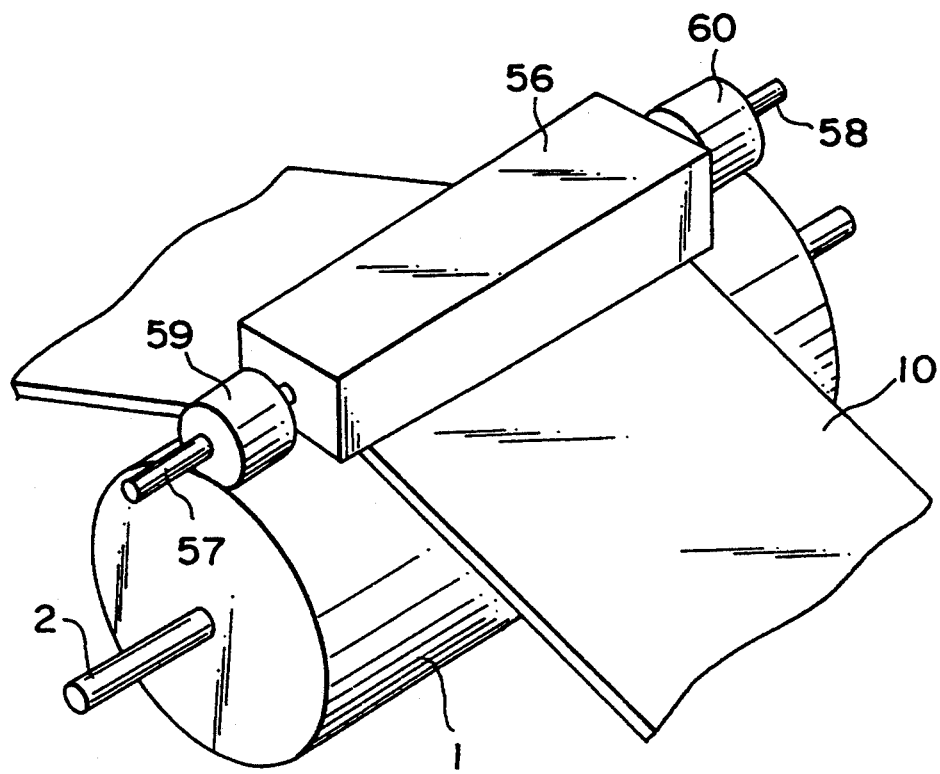
FIG. 22B is a perspective view of the apparatus.

FIG. 22A is a cross-sectional front view showing an important portion of a magnetic inspection apparatus according to still another embodiment of the present invention, and FIG. 22B shows an external appearance of this apparatus. The same parts as in the embodiment of FIG. 1 are denoted by like reference numerals, and detailed descriptions of the common parts are omitted.

According to this embodiment, a pair of rollers 59 and 60 of, e.g. rubber are attached via shafts 57 and 58 on both sides of a support frame 56 storing the magnetic sensor array 7 facing the thin steel strip 10 and the shield plates provided on both sides of the array 7. The rubber rollers 59 and 60 are put in contact with outer peripheral edge portions of the hollow roll 1.

In the magnetic inspection apparatus with this structure, the lift-off L (or the distance) between the magnetic sensor array 7 and the surface of the thin steel strip 10 is kept at a constant value determined by the outside diameter of each roller 59, 60 and the shape of the support frame 56. Accordingly, the magnetic sensor array 7 is not influenced by vibration due to running of the thin steel strip 10.

Like the embodiment of FIGS. 20 and 21, the horizontal movement of the support frame 56 is restricted by a support mechanism (not shown) so as to keep a predetermined relationship between the magnetic sensor array 7 and the magnetic poles 4a and 4b.

Figure 23:
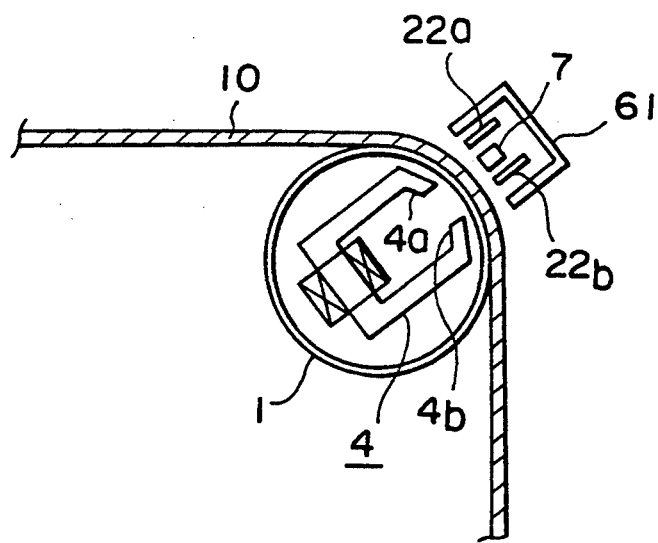
FIG. 23 is a cross-sectional view showing a magnetic inspection apparatus according to still another embodiment of the invention.

FIG. 23 is a cross-sectional side view showing an important portion of a magnetic inspection apparatus according to still another embodiment of the present invention. The same parts as in the embodiment of FIG. 1 are denoted by like reference numerals, and detailed descriptions of the common parts are omitted.

In this embodiment, the thin steel strip 10 is wound around the hollow roll 1 storing the magnetizer 4 over about 90° with a predetermined tensile force applied. A support frame 61 storing the magnetic sensor array 7 and shield plates 22a and 22b is situated outside the hollow roll 1 so as to face the magnetic poles 4a and 4b of the magnetizer 4.

According to the magnetic inspection apparatus having the above structure, the angle of contact of the thin steel strip 10 with the hollow roll 1 is very large, i.e. 90°. Thus, vibration of the thin steel strip 10 is remarkably damped while the steel strip 10 is being in contact with the hollow roll 1. Therefore, the lift-off L between the magnetic sensor array 7 and steel plate 10 can be decreased, and the magnetic inspection sensitivity and S/N can be enhanced.

Figure 24:
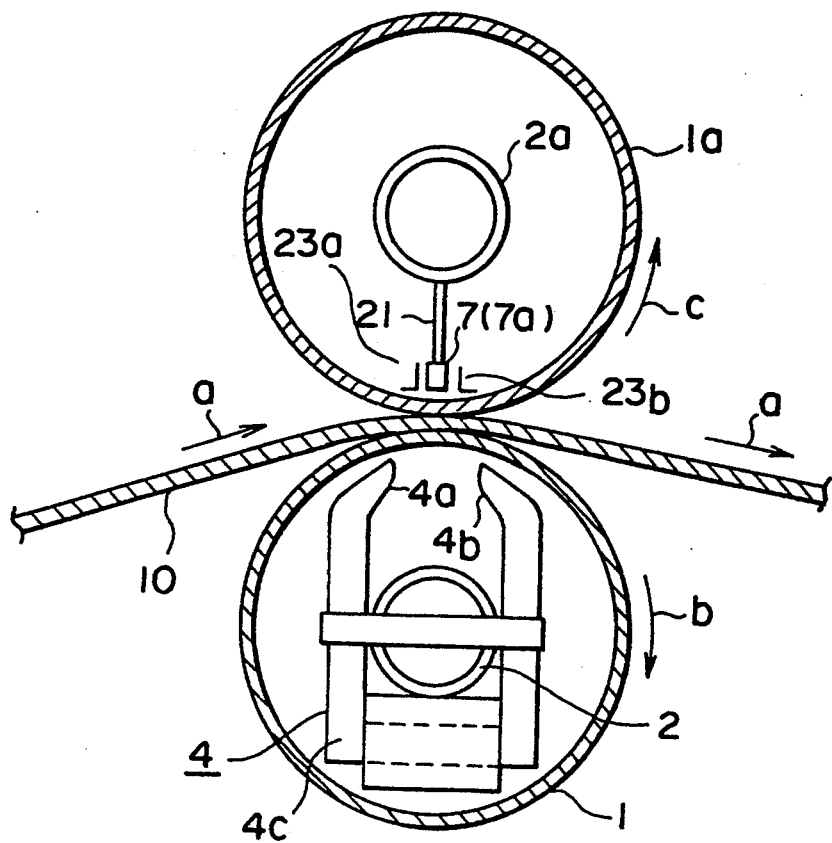
FIG. 24 is a cross-sectional view showing a magnetic inspection apparatus according to still another embodiment of the invention.

FIG. 24 is a cross-sectional view schematically showing the structure of the magnetic inspection apparatus according to still another embodiment of the invention. The same parts as in the embodiment of FIG. 1 are denoted by like reference numerals, and detailed description of the common parts is omitted.

Figure 25:
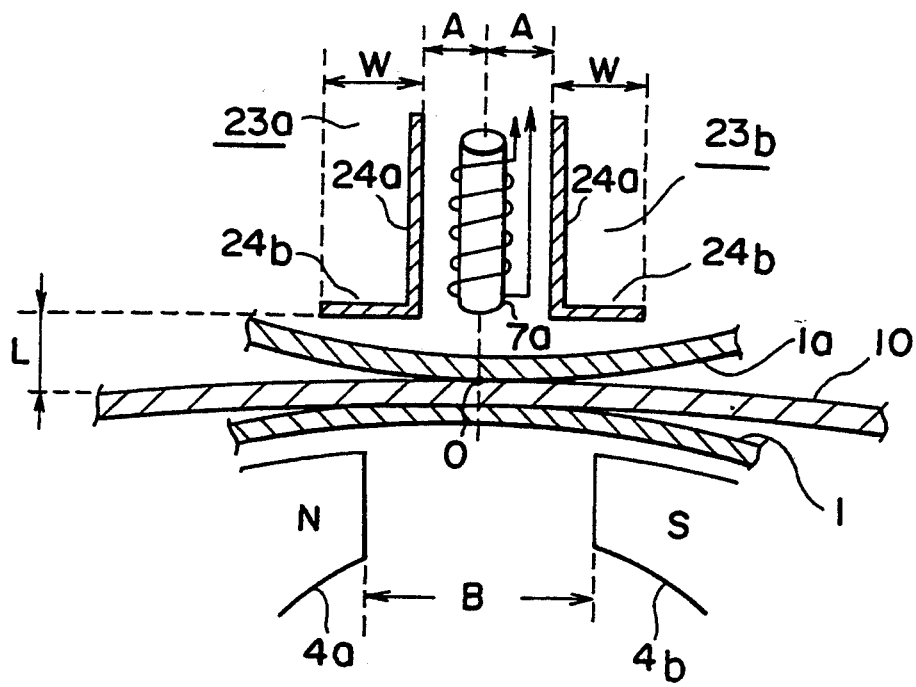
FIG. 25 is a partly enlarged view showing an important portion of the apparatus.

In this embodiment, shield plates 23a and 23b each having an L-cross section are supported by support members (not shown) on both sides of the magnetic sensor 7a in the upper hollow roll 1a, which are opposed to the magnetic poles 4a and 4b. Each of the shield plates 23a and 23b has the same shape as the shield plate 23 shown in FIG. 9. As shown in FIG. 25, each of the shield plates 23a and 23b has a vertical portion 24a with a height H in a direction perpendicular to the thin steel strip 10, and a horizontal portion 24b with a width W in a direction parallel to the steel strip 10. Each shield plate 23a, 23b has a thickness t. Each shield plate 23a, 23b is situated at a distance A from the magnetic sensor array 7. The lower ends of the shield plates 23a and 23b are substantially on a level with the lower end of each magnetic sensor 7a.

In this apparatus, the length D of each magnetic sensor 7a is 5 mm, the height H of each shield body 23a, 23b is 16 mm, and the thickness of each shield body is 0.2 mm. The width W of the horizontal portion 24b is 6 mm. The distance A between each shield body 23a, 23b and the center axis of each magnetic sensor 7a is 4 mm. The lift-off L represented by the distance between the thin steel strip 10, on one hand, and each magnetic sensor 7a and each shield body 23a, 23b, on the other hand, is 3.6 mm. The length of each shield plate 23a, 23b in the axial direction of the hollow roll 1 is greater than that of the magnetic sensor array 7. Further, the inter-magnetic pole distance B of the magnetizer 4 is 15 mm.

The relationship between the inter-shield plate distance 2A and width W of horizontal portion 24b of each shield plate 23a, 23b with the L-cross section and lift-off L and inter-magnetic pole distance B will now be described. Specifically, the vertical component of the magnetic field obtained by the magnetic sensor 7a when the dimensions and position of the shield plates 23a and 23b are varied were computer-simulated.

Figure 26:
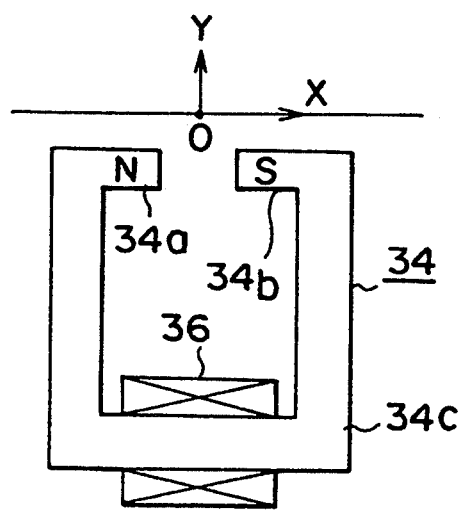
FIG. 26 shows a test model for use in a simulation for obtaining numerical values in the invention.

Suppose a test model of the magnetizer 34 with the shape as shown in FIG. 26. Like the magnetizer shown in FIGS. 13 and 14, the distance B between the magnetic poles 34a and 34b is variable between 10 mm, 20 mm and 30 mm. The thickness of each steel plate forming a magnetizing core 34c is 0.4 mm. The current density of a current flowing in a magnetizing coil 36 is $1.25 \times 10^5$ A/m² is 3 mm. A center point O of the thin steel strip 10 or the object to be inspected is the original point of (X, Y) coordinates.

Figure 27:
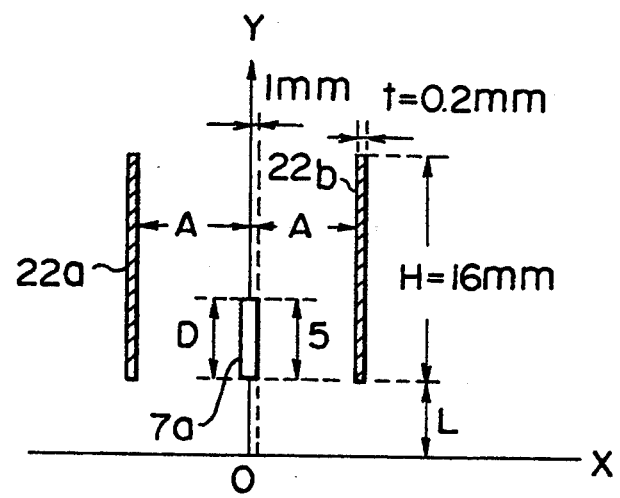
FIG. 27 shows an arrangement of shield plates for use in the simulation.
Figure 28:
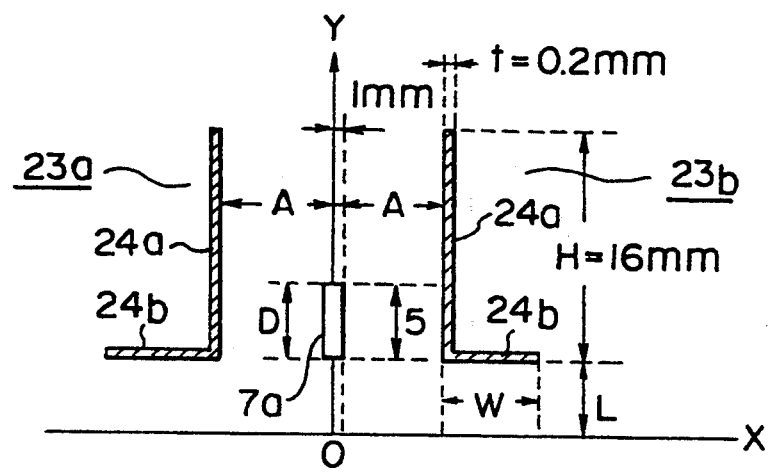
FIG. 28 shows an arrangement of other shield plates for use in the simulation.

Suppose that the shield plates 22a and 22b having only vertical portions without horizontal portions, as shown in FIG. 27, and the shield plates 23a and 23b having both vertical portions 24a and horizontal portions 24b, as shown in FIG. 28, are located in the (X, Y) coordinates. The length D of the magnetic sensor 7a provided between the shield plates 22a and 22b (23a and 23b) is 5 mm.

It is supposed that there are two samples of the object to be inspected (i.e. the thin steel strip 10), one being free of defects and the other having a standard defect of 0.4 mm in diameter.

Using the test models of the magnetizer and shield plates, the vertical component of the magnetic field was calculated, which is obtainable by the magnetic sensor 7a while varying the parameters: the distance A between the shield plates 22a to 23b and the center of the magnetic sensor 7a, the lift-off L, the inter-magnetic pole distance B, the presence/absence of shield plates 22a to 23b, and the presence/absence of a defect in the to-be-inspected object. Since the magnetic sensor 7a has the length D (=5 mm), the vertical component at every 1 mm in the vertical direction is integrated from 0 mm to 5 mm, thereby obtaining the vertical component of the magnetic field. The vertical component of the magnetic field at distance X=0 is replaced with the values at X=1 mm. Further, when the sample with the standard defect is used, it assumed that the defect is located at the original point O.

Figure 29B:
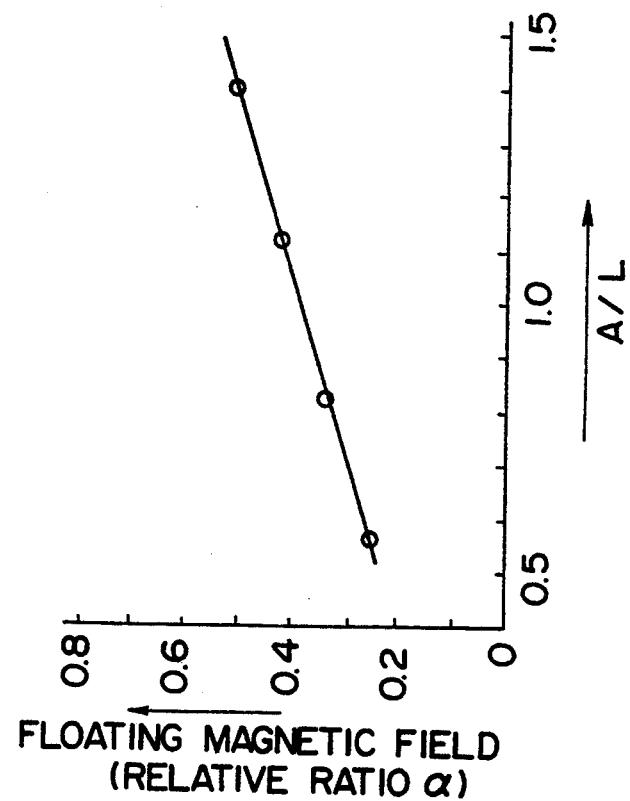
FIG. 29B shows a magnetic field characteristic indicating the simulation result associated with the shield shape shown in FIG. 27.
Figure 29A:
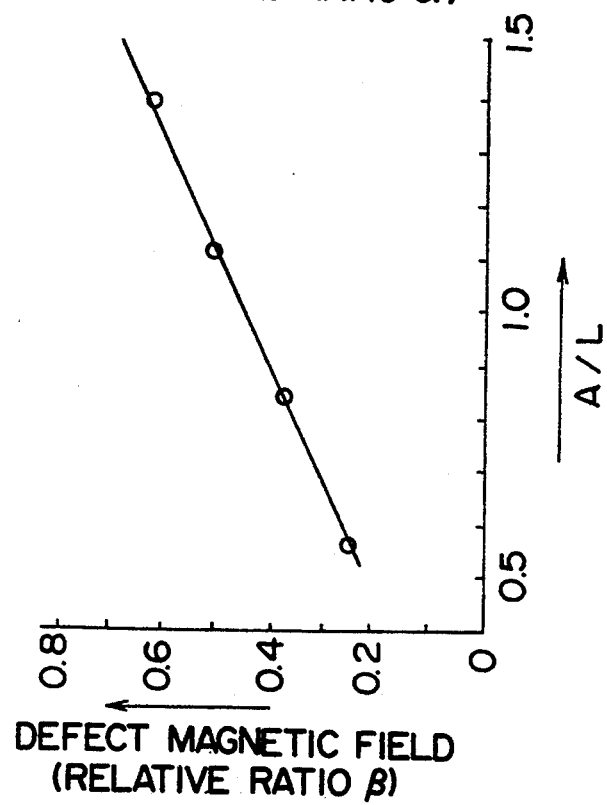
FIG. 29A shows a magnetic field characteristic indicating the simulation result associated with the shield shape shown in FIG. 27.

FIG. 29A shows a ratio $\beta$ between a magnetic field (vertical component) $\beta 1$ in the case where the shield plates 23a and 23b are provided and a magnetic field (vertical component) $\beta 2$ in the case where the shield plates 23a and 23b are not provided, under the condition that the sample with the standard defect is used. The horizontal axis of FIG. 29A indicates (A/L). That is, FIG. 29A shows the relative ratio $\beta$ of the defect magnetic field, depending on the presence/absence of the shield.

On the other hand, FIG. 29B shows a ratio a between a magnetic field (vertical component) $\alpha 1$ in the case where the shield plates 23a and 23b are provided and a magnetic field (vertical component) $\alpha 2$ in the case where the shield plates 23a and 23b are not provided, under the condition that the defect-free sample is used. The horizontal axis of FIG. 29B indicates (A/L). That is, FIG. 29B shows the relative ratio $\alpha$ of the defect magnetic field, depending on the presence/absence of the shield.

Figure 30:
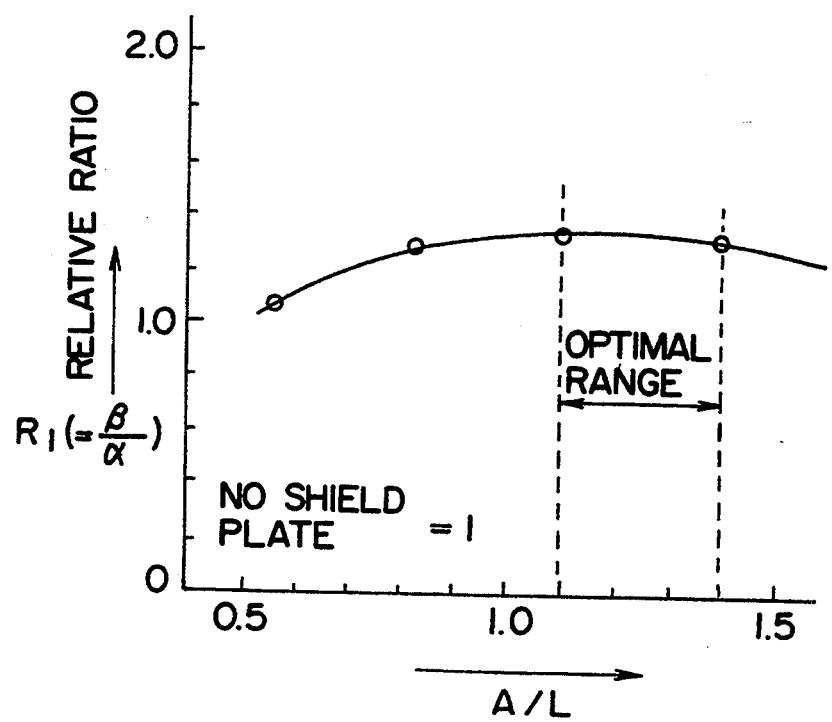
FIG. 30 shows another magnetic field characteristic indicating the simulation result.

A relative ratio R1 ($=\beta/\alpha$) indicated by relative ratio a of FIG. 29B and relative ratio $\beta$ of FIG. 29A is calculated. FIG. 30 shows the relative ratio R1 ($=\beta/\alpha$), with the horizontal axis thereof indicating (A/L). The relative ratio R1 in the state in which the shield plates 22a and 22b are not provided is set at 1.

Specifically, FIG. 30 shows the ratio R1 between the magnetic field ($\beta$), in which the leakage magnetic flux due to the defect and the floating magnetic flux are added, and the magnetic field ($\alpha$) of only the floating magnetic flux. Thus, the higher the relative ratio R1, the higher the ratio of the leakage magnetic field due to the defect included in the magnetic field detected by the magnetic sensor 7a.

Accordingly, it is understood that the optimal range of the ratio (A/L) of the half distance A of the distance 2A between the shield plates 22a and 22b to the lift-off L is 1:1 to 1.4 expressed by formula (1).

Figure 31B:
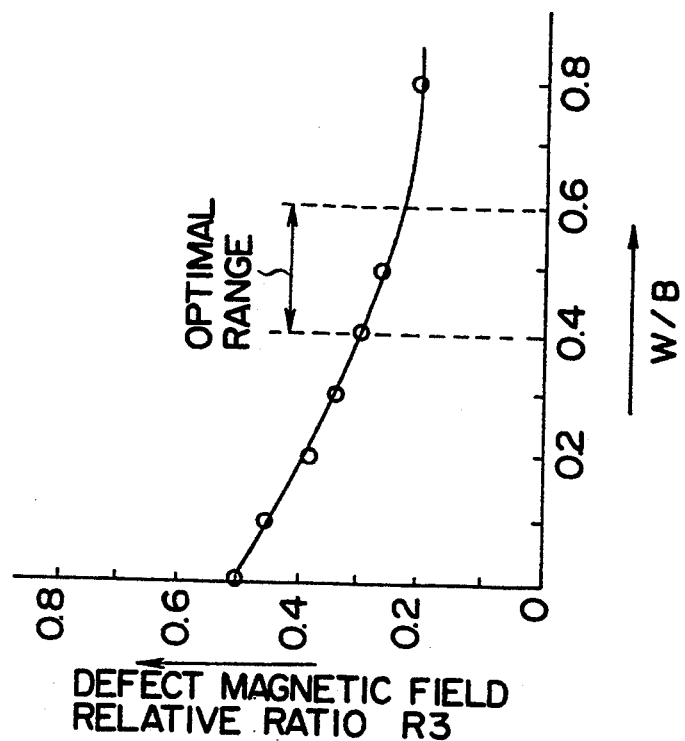
FIG. 31B shows a defect magnetic field characteristic indicating the simulation result associated with the shield shape shown in FIG. 28.
Figure 31A:
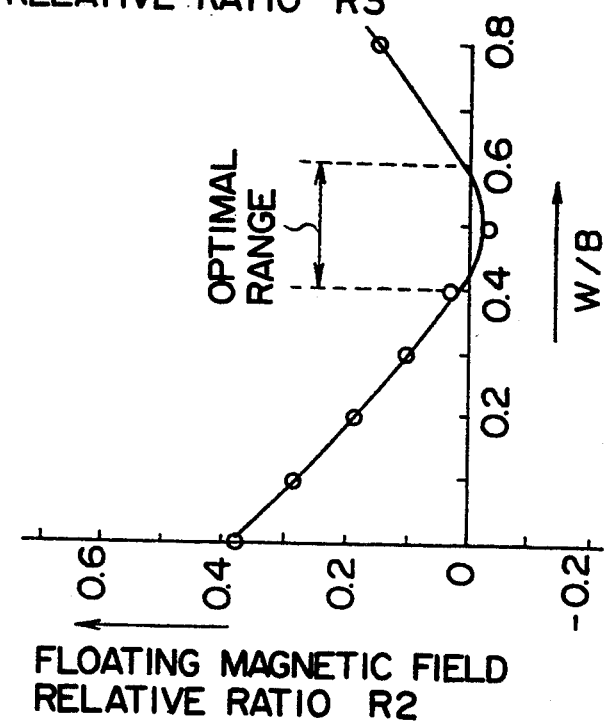
FIG. 31A shows a floating magnetic field characteristic indicating the simulation result associated with the shield shape shown in FIG. 28.

FIG. 31A shows a relative ratio R2 ($=\gamma 1/\gamma 2$) of a floating magnetic flux $\gamma 1$ in the magnetic sensor 7a, in the case where the L-cross sectional shield plates 23a and 23b with horizontal portions 24b are used, to a floating magnetic flux $\gamma$ in the case where the shield plates 23a and 23b are not provided under the same condition, when the defect-free sample is used. The horizontal axis of FIG. 31A indicates (W/B). That is, FIG. 31A shows a relative ratio R2 of the floating magnetic flux, depending on the presence/absence of the shield.

The direction of the vertical component of the magnetic field intersecting the magnetic sensor 7a may change to an upward direction or a downward direction, depending on the presence/absence of the shield plates 23a and 23b. As a result, when the relative ratio R2 ($=\gamma 1/\gamma 2$) is calculated, the calculated value may be a ($-$) value. Thus, the region of the ($-$) value is evaluated by an absolute value.

Accordingly, in FIG. 31A, in the region where the relative ratio R2 ($=\gamma 1/\gamma 2$) is low, the ratio of the floating magnetic field in the magnetic field detected by the magnetic sensor 7a is very low due to the presence of the shield plates 23a and 23b. Thus, the region where the relative value R2 ($=\gamma1/\gamma2$) is low is set to be an optimal range.

FIG. 31B shows a relative ratio R3 ($=\delta1/\delta2$) of a magnetic field $\delta1$ in the magnetic sensor 7a, in the case where the shield plates 23a and 23b are provided, to a magnetic field $\delta2$ in the case where the shield plates 23a and 23b are not provided, under the condition that the sample with the standard defect is used. The horizontal axis of FIG. 31B indicates (W/B). Accordingly, FIG. 31B shows the relative value R3 of the magnetic field including the floating magnetic flux and the leakage magnetic flux due to the defect, depending on the presence/absence of the shield.

Specifically, FIG. 31B shows that the ratio of the leakage magnetic flux in the detected magnetic field becomes higher in accordance with the increase in relative ratio R3 ($=\delta1/\delta2$). It is thus understood that a lower (W/B) is advantageous.

Comparing the characteristic of FIG. 31A and that of FIG. 31B, the optimal relationship between the width W of the horizontal portion 24b of each shield plate 23a, 23b and the inter-magnetic pole distance B is expressed by $0.4 \leq W/B \leq 0.6$ of formula (2).

Figure 32:
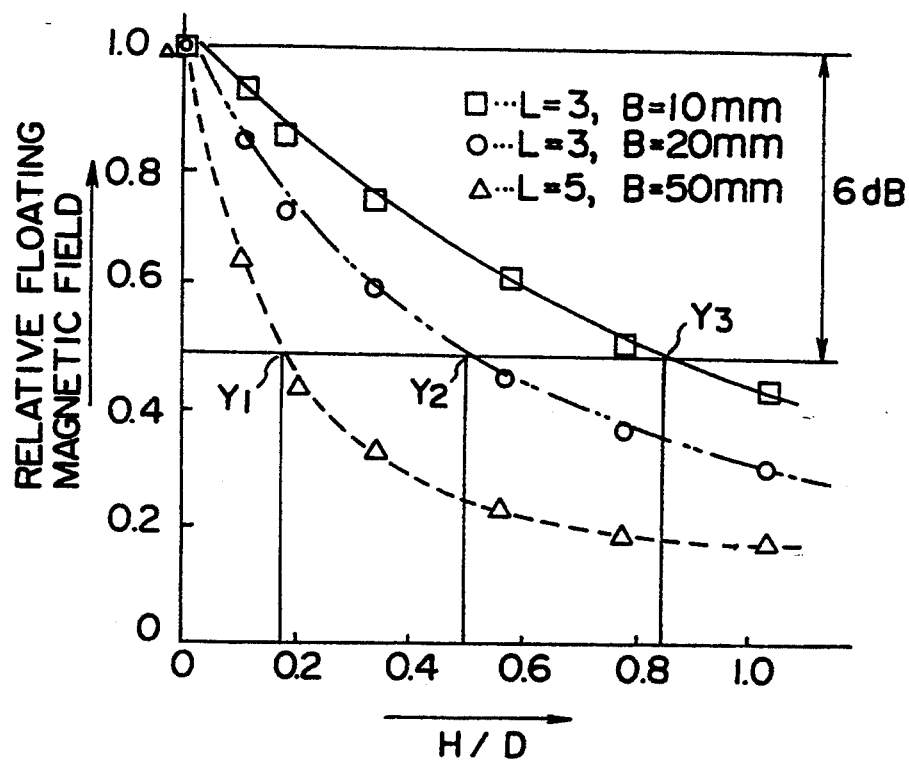
FIG. 32 shows a relative floating magnetic field characteristic indicating the simulation result.

FIG. 32 shows the simulation result of the vertical component of the magnetic field detected by the magnetic sensor 7a in the case where the defect-free sample was used and the ratio (H/D) of the height H of the magnetic shield 22a, 22b to the length D of the magnetic sensor 7a was varied. The lift-off L and inter-magnetic pole distance B were used as parameters.

Figure 33:
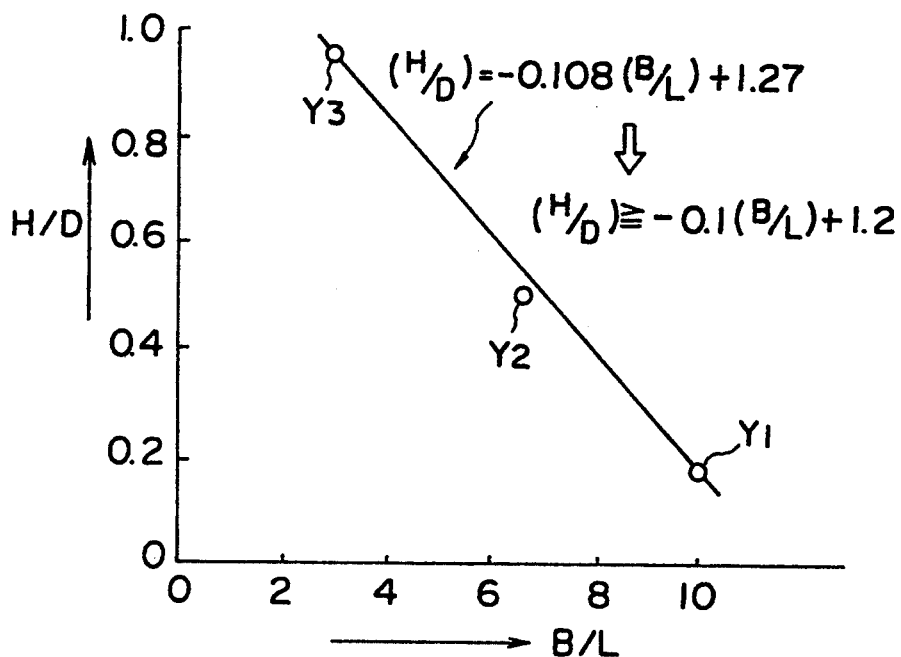
FIG. 33 shows an optimal characteristic indicating the simulation result.

According to FIG. 32, when the height H of the shield plate 22a, 22b is increased, the floating magnetic field detected by the magnetic sensor 7a decreases. For example, when a region having a magnetic field level lower than a reference level by 6 dB or more is set to be an allowable range of floating magnetic field, values of the ratio (H/D) at locations where the characteristic lines intersect the −6 dB line are Y1, Y2 and Y3. Y1, Y2 and Y3 can be approximated by the characteristic of FIG. 33, when the horizontal axis indicates the ratio (B/L). This characteristic is linearly approximated by formula (5):

$$(H/D) = -0.108(B/L) + 1.27 \quad (5)$$

The allowable range is above the linear characteristic line of formula (5). It is thus desirable that the relationship (H/D) between the height H of the shield plate 22a, 22b and the height D of the magnetic sensor 7a be set at a value determined by formula (6) with use of the ratio (B/L) of the inter-magnetic pole distance B and lift-off L.

$$(H/D) \leq -0.1(B/L) + 1.2 \quad (6)$$

As has been described above, the shield plates 22a to 23b are provided on both sides of the magnetic sensor 7a and the relationship between the width of each shield plate, height H of each shield plate, distance 2A between the shield plates, inter-magnetic pole distance B of the magnetizer, lift-off L, and height D of the magnetic sensor 7a is determined by formulae (1), (2) and (3). Thereby, the floating magnetic flux component in the magnetic field detected by the magnetic sensor 7a can be decreased, and only the leakage magnetic flux component due to the defect can be remarkably increased. Thus, saturation of the output of the magnetic sensor 7a can be prevented, the defect detection sensitivity increased, and the detection precision enhanced.

The present invention is not limited to the above embodiments. In the apparatuses of the embodiments, the magnetic sensor array 7 is provided within the upper hollow roll 1a. However, the shield plates 22a and 22b, for example, may be provided on both sides of the magnetic sensor array 7 within the hollow roll 1 of the conventional apparatus shown in FIG. 39.

In the embodiments, the shield plates 22a and 22b or L-cross sectional shield plates 23a and 23b are provided on both sides of the magnetic sensor array 7. However, for example, a cylindrical shield body surrounding the entire magnetic sensor array 7 may be provided.

Figure 34:
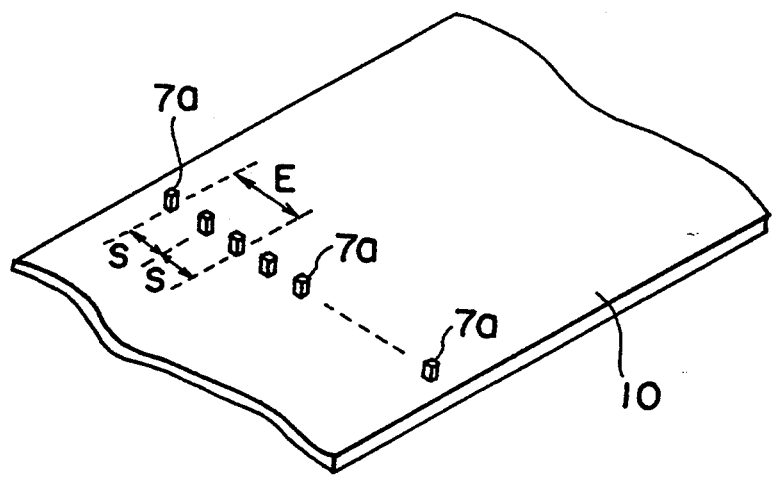
FIG. 34 shows an arrangement of magnetic sensors in a magnetic inspection apparatus according to still another embodiment of the invention.

FIG. 34 shows schematically an important portion of a magnetic inspection apparatus according to another embodiment of the present invention. This apparatus has the same structure as shown in FIGS. 1, 2 and 3. A number of magnetic sensors 7a are arranged within the upper hollow roll 1, as shown in FIG. 34, at regular intervals S in the width direction of the thin steel strip 10.

Figure 35:
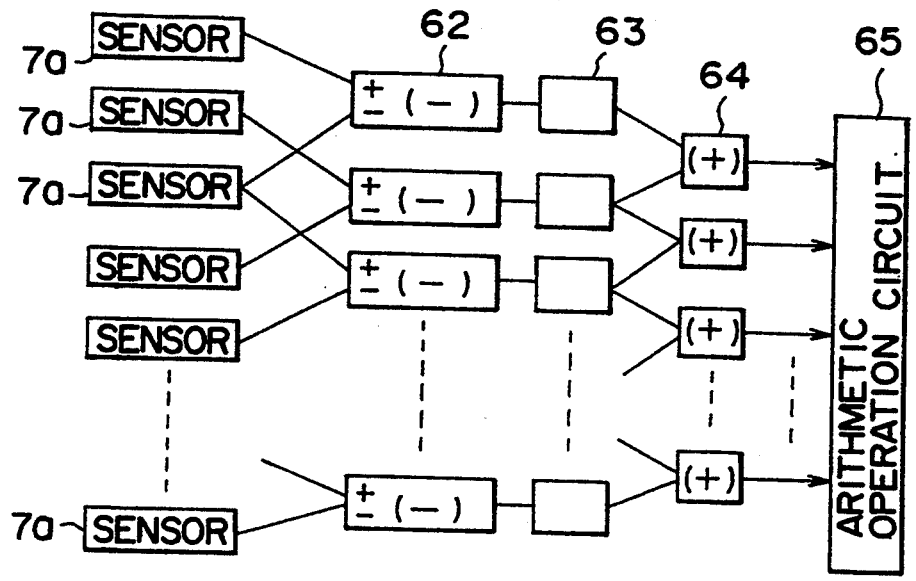
FIG. 35 is a block diagram showing an electric structure of the apparatus.

FIG. 35 is a block diagram showing an electric structure of the apparatus of this embodiment.

Outputs from the magnetic sensors 7a are input to subtraction circuits 62. Each subtraction circuit 62 receives a pair of output signals from a pair of magnetic sensors with another magnetic sensor interposed therebetween, arranged in the width direction of the thin steel strip 10. The subtraction circuit 62 subtracts one output signal from the other output signal and outputs a difference signal. Difference signals from the subtraction circuits 62 are input to absolute value circuits 63. The absolute value circuits 63 calculate absolute values of the input difference signals and output absolute value signals. The absolute value signals output from the absolute value circuits 63 are input to summing circuits 64.

Each summing circuit 64 sums absolute value signals from adjacent two absolute value circuits 63 and delivers a sum signal to an arithmetic operation circuit 65. The arithmetic operation circuit 65 calculates the defect position in the width direction of the thin steel strip 10 and defect magnitude on the basis of the signal level of each sum signal input from the summing circuits 64. The calculated defect position and defect magnitude are output to an output device (not shown) such as a CRT display device.

In the magnetic inspection apparatus with the above structure, each subtraction circuit 62 outputs a difference signal representing a difference between output signals from two magnetic sensors 7a arranged in the width direction at a distance E ($=2S$) from each other. The absolute value of the difference signal is calculated by the absolute value circuit 63.

As stated above, local non-uniformity in magnetic permeability occurs in the to-be-inspected body due to internal stress, non-uniformity in material quality, a variation in thickness of the object, etc. caused at the time of processing the steel strip. Accordingly, a variation component of leakage magnetic flux due to non-uniform magnetic permeability is included as noise in the detection signal of the magnetic sensor.

In general, an area of non-uniformity of magnetic permeability is much greater than an area of a defect. Thus, the variation component of the leakage magnetic flux due to non-uniform magnetic permeability is detected simultaneously by two magnetic sensors 7a. On the other hand, the leakage magnetic flux due to the defect has such a magnitude as can be detected by one magnetic sensor 7a. Thus, if a difference signal representing a difference between output signals from every two magnetic sensors 7a arranged with another magnetic sensor interposed, as shown in the figures, is obtained, noise component due to non-uniform magnetic permeability can be removed from the difference signal. Therefore, the S/N of the output signal of the magnetic sensor 7a is improved.

Figure 36:
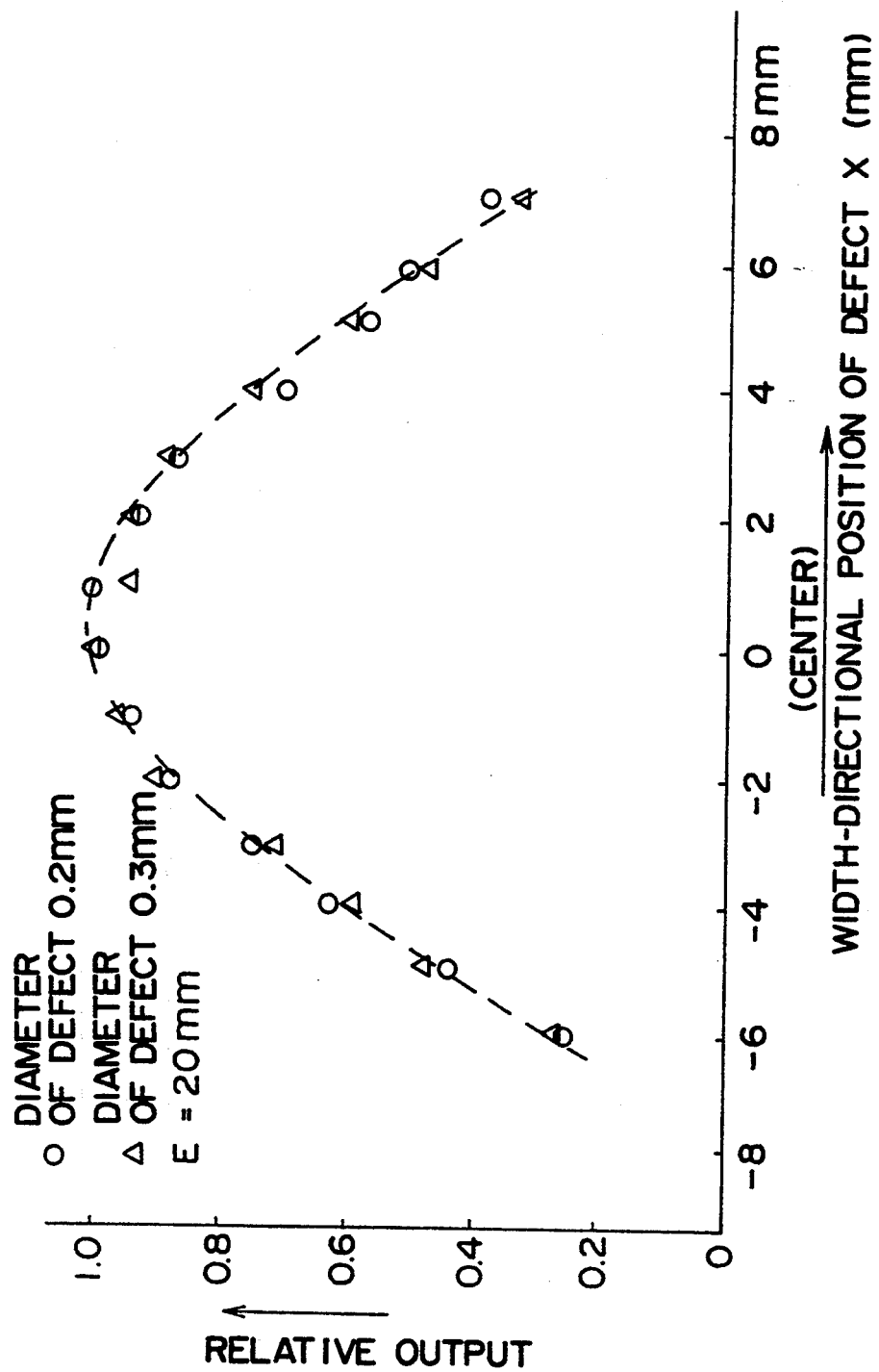
FIG. 36 shows the relationship between the position of the magnetic sensors and the output in the apparatus.

In order to confirm the advantage of this embodiment, the inventors conducted actual inspection tests on two types of thin steel strips 10 made for tests, which have defects of 0.2 mm and 0.3 mm in diameter. The interval S of the magnetic sensors 7a is 10 mm. Thus, the distance E between the two magnetic sensors 7a whose output signals are supplied to the corresponding subtraction circuit 62 is 20 mm. Output signals are delivered from the summing circuits 64 at width-directional positions x, when the position of the defect of the two types of thin steel strips for tests is displaced from the center of one magnetic sensor 7a in opposite directions along the width in units of 1 mm (6 mm in each direction, and 12 mm in total). FIG. 36 shows the relationship between each width-directional position of the defect and the relative value of the output signal.

Figure 37:
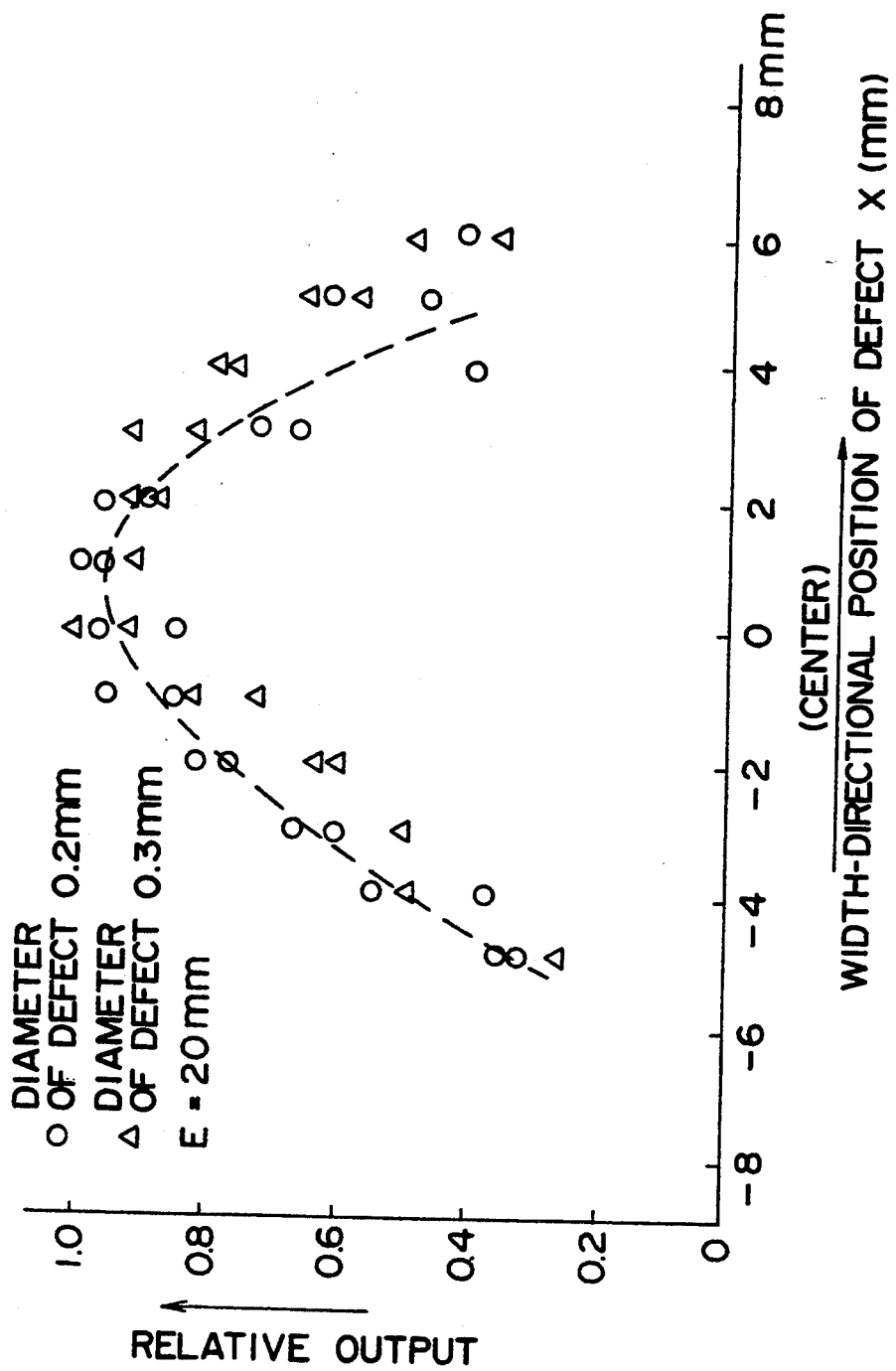
FIG. 37 shows the relationship between the position of the magnetic sensors and the output in a conventional apparatus.

FIG. 37 shows the relationship between each width-directional position of the defect and the relative value of the output signal when the subtraction circuits 62, absolute value circuits 63 and summing circuits 64 are removed and the detection signals from the magnetic sensors 7a are directly delivered to the arithmetic operation circuit 65. As shown in FIGS. 36 and 37, by adopting the structure of this embodiment, the measurement error at the same defect position can be remarkably reduced. As a result, the S/N of the output signals is greatly improved.

Regarding the arrangement of the magnetic sensors 7a shown in FIG. 34, if the distance E between the two magnetic sensors 7a for calculating the difference signal is too small, both magnetic sensors 7a undesirably detect the leakage magnetic flux due to the same defect. Inversely, if the distance E between the magnetic sensors 7a is too large, it is difficult to detect a common leakage magnetic flux due to the non-uniform magnetic permeability. Accordingly, there is an optimal range of the distance E between the magnetic sensors.

Further, if the lift-off between the magnetic sensors 7a and the thin steel strip 10 is too great, the S/N lowers. Thus, the optimal range of the distance E between the magnetic sensors relates to the lift-off.

Figure 38:
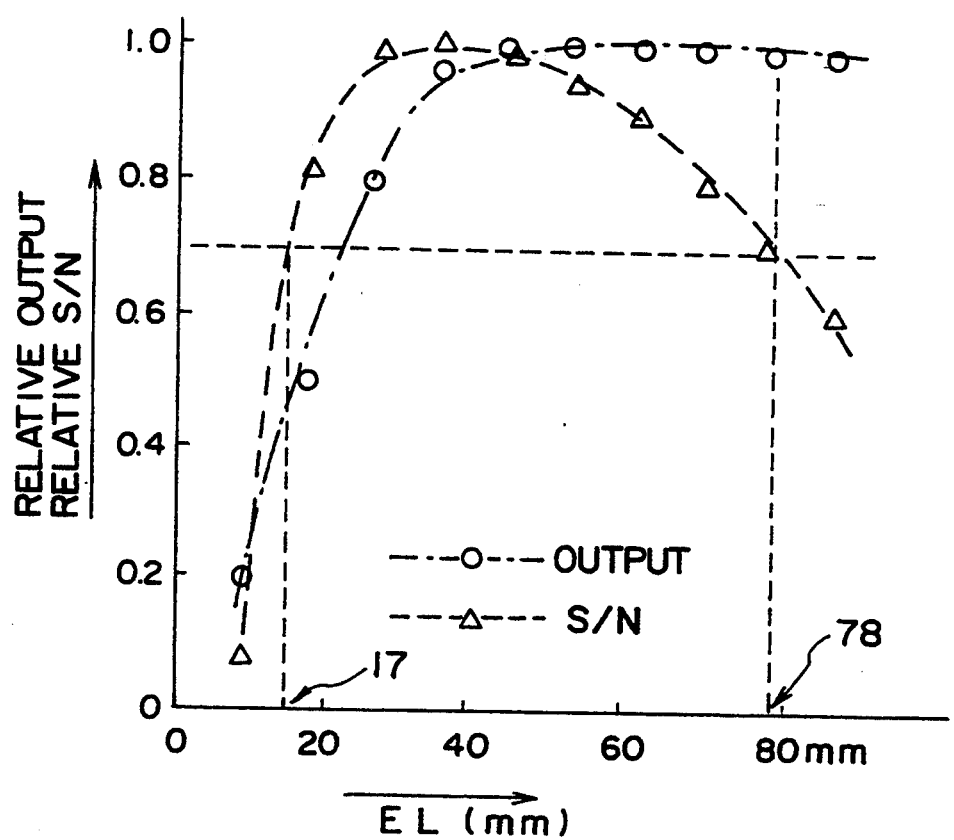
FIG. 38 shows the relationship between the interval of the magnetic sensors and the output in the apparatus of the embodiment.

FIG. 38 shows the relationship between a value (EL) obtained by multiplying the lift-off L by the distance E between magnetic sensors 7a, and a relative output of a sum signal input to the arithmetic operation circuit 65 at each value EL (mm) and a relative S/N of the sum signal.

As shown in FIG. 38, in the case where the lift-off L is constant, when the distance E increases, the relative output increases up to a fixed saturation value. However, if the distance E increases, the relative S/N decreases to the contrary. Accordingly, if a practically sufficient allowable range of the relative S/N and relative output value is 0.7 or more, an optimal range of the value (EL) is 17 to 78 expressed by formula (7):

$$17 \leq EL \leq 78 \quad (7)$$

For example, if the lift-off L is set at 3 mm, the optimal range of the distance E between the magnetic sensors is 6 to 16 mm.

In the embodiment shown in FIG. 35, the subtraction circuits 62, absolute value circuits 63 and summing circuits 64 are constituted by ordinary analog circuits. However, these circuits may be constituted by, e.g. digital circuits.

As described above, the distance E between the magnetic sensors for calculating the difference signal is set at a value determined by formula (7) in accordance with the lift-off L. Thereby, the noise component due to the non-uniform permeability in the thin steel strip 10 can be eliminated and a small defect in the steel strip 10 can be detected with a high S/N.

We claim:

1. A magnetic inspection apparatus comprising:
   magnetizer means for generating a magnetic field in an object to be inspected, said object running in a predetermined direction, said magnetizer means including a pair of magnetic poles provided in facing relation to said object, said pair of magnetic poles being arranged in said predetermined direction;
   a plurality of magnetic sensor means, arranged at small intervals in a widthwise direction of said object perpendicular to said predetermined direction, for detecting a leakage magnetic flux due to a defect of said object at locations in said widthwise direction, each said magnetic sensor means having sides which face said magnetic poles;
   a pair of shield plates, each shield plate having a low coercive force and |-shaped cross-sectional configuration, situated in facing relation to said sides of said magnetic sensor means which face said magnetic poles and arranged in said widthwise direction of said object; and
   the distance between said shield plates being set between 2.2 and 2.8 times the distance between said magnetic sensor means and said object.

2. The apparatus according to claim 1, wherein each of said magnetic sensor means includes a vertical type magnetic sensor means for detecting a vertical component of the leakage magnetic flux due to the defect, which component intersects the surface of the object at right angles.

3. The apparatus according to claim 2, wherein a relationship between a distance 2A between said shield plates and a distance B between said magnetic poles is defined by:

$$-0.01B + 0.55 \leq 2A \leq -0.01B + 0.65.$$

4. The apparatus according to claim 2, wherein a relationship between a height D of the magnetic sensor means in a direction perpendicular to the object, a height H of each shield plate in the direction perpendicular to the object, a distance 2A between the shield plates, a distance B between the magnetic poles, and a distance L between the magnetic sensor means and the object is defined by:

$$(H/D) \leq -0.1(B/L) + 1.2.$$

5. The apparatus according to claim 1, further comprising a stationary shaft extending at right angles with a running path of the object and a hollow roll rotatably supported on said stationary shaft so as to rotate when the hollow roll is put in contact with the surface of the object running along the running path, and wherein said magnetizer means is situated within said hollow roll.

6. The apparatus according to claim 5, further comprising:
   support frame means having a -cross section, for supporting said pair of shield plates and said magnetic sensor means arranged between said shield plates; and
   a plurality of roller means journaled at lower end portions of said support frame, for supporting said support frame means on the surface of said running object.

7. The apparatus according to claim 5, further comprising:
   support frame means having a -cross section, for supporting said pair of shield plates and said magnetic sensors arranged between said shield plates; and
   a plurality of roller means journaled at both end portions of said support frame means, for supporting said support frame means on a peripheral surface of said hollow roll in a rotating state.

8. A magnetic inspection apparatus comprising:
   magnetizer means for generating a magnetic field in an object to be inspected, said object running in a predetermined direction, said magnetizer means having a pair of magnetic poles provided in facing relation to said object, said pair of magnetic poles being arranged in said predetermined direction;
   a plurality of magnetic sensor means, arranged at small intervals in a widthwise direction of said object perpendicular to said predetermined direction, for detecting a leakage magnetic flux due to a defect of said object at locations in said widthwise direction, each said magnetic sensor means having sides which face said magnetic poles;
   a pair of shield plates, each shield plate having a low coercive force, situated in facing relation to said sides of said magnetic sensor means which face said magnetic poles and arranged in said widthwise direction of said object, each of said shield plates having an L-shaped cross-sectional configuration comprised of a vertical portion extending in a direction perpendicular to said object, and a horizontal portion attached to an end portion of said vertical portion facing said object, said horizontal portion extending towards an adjacent one of said magnetic poles; and
   the distance between said shield plates being set between 2.2 and 2.8 times the distance between said magnetic sensor means and said object.

9. The apparatus according to claim 8, wherein each of said magnetic sensor means includes a vertical type magnetic sensor means for detecting a vertical component of the leakage magnetic flux due to the defect, which component intersects the surface of the object at right angles.

10. The apparatus according to claim 9, wherein the width of the horizontal portion of each of the shield plates in the direction of arrangement of the magnetic poles is set between 0.4 and 0.6 times the distance between the magnetic poles.

11. A magnetic inspection apparatus comprising:
    magnetizer means for generating a magnetic field in an object to be inspected, said magnetizer means having a pair of magnetic poles provided in facing relation to said object;
    a plurality of magnetic sensor means for detecting a leakage magnetic flux due to a defect of said object, each said magnetic sensor means having sides which face said magnetic poles;
    a pair of shield plates, each shield plate having a low coercive force, situated in facing relation to said sides of said magnetic sensor means which face said magnetic poles; and
    wherein each of said shield plates has an L-shaped cross-sectional configuration comprised of a vertical portion extending in a direction perpendicular to said object, and a horizontal portion attached to an end portion of said vertical portion facing said object, said horizontal portion extending towards an adjacent one of said magnetic poles.

12. The apparatus according to claim 11, wherein each of said magnetic sensor means includes a vertical type magnetic sensor means for detecting a vertical component of the leakage magnetic flux due to the defect, which component intersects the surface of the object at right angles.

13. The apparatus according to claim 12, wherein the distance between said shield plates is set between 2.2 and 2.8 times the distance between said magnetic sensor means and said object.

14. The apparatus according to claim 12, wherein the width of the horizontal portion of each of the shield plates in the direction of arrangement of the magnetic poles is set between 0.4 and 0.6 times the distance between the magnetic poles.

* * * * *